(12) United States Patent
Albrecht et al.

(10) Patent No.: US 8,961,410 B2
(45) Date of Patent: *Feb. 24, 2015

(54) SURGICAL RETRACTOR WITH GEL PAD

(75) Inventors: Jeremy J. Albrecht, Rancho Santa Margarita, CA (US); Jennifer T. Ko, Vista, CA (US); Gary M. Johnson, Rancho Santa Margarita, CA (US); John R. Brustad, Rancho Santa Margarita, CA (US); Kevin K. Dang, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 351 days.

This patent is subject to a terminal disclaimer.

(21) Appl. No.: 13/345,279

(22) Filed: Jan. 6, 2012

(65) Prior Publication Data

US 2012/0108906 A1 May 3, 2012

Related U.S. Application Data

(63) Continuation of application No. 12/119,371, filed on May 12, 2008, now Pat. No. 8,109,873.

(60) Provisional application No. 60/917,580, filed on May 11, 2007.

(51) Int. Cl.
*A61B 1/32* (2006.01)
*A61B 17/34* (2006.01)
*A61B 17/00* (2006.01)

(52) U.S. Cl.
CPC ............... *A61B 1/32* (2013.01); *A61B 17/3423* (2013.01); *A61B 17/3431* (2013.01); *A61B 17/3462* (2013.01); *A61B 2017/00477* (2013.01); *A61B 2017/3435* (2013.01)

USPC .......................................... 600/208; 600/210

(58) Field of Classification Search
USPC ......... 600/201–246; 138/109, 22.11; 277/613
See application file for complete search history.

(56) References Cited

U.S. PATENT DOCUMENTS

| | | |
|---|---|---|
| 558,364 A | 4/1896 | Doolittle |
| 1,157,202 A | 10/1915 | Bates et al. |

(Continued)

FOREIGN PATENT DOCUMENTS

| | | |
|---|---|---|
| DE | 26 05 148 A1 | 8/1977 |
| DE | 33 36 279 C2 | 1/1986 |

(Continued)

OTHER PUBLICATIONS www.thefreedictionary.com/strand, definition of "strand" accessed Jul. 18, 2014.*

(Continued)

*Primary Examiner* — Jan Christopher Merene
(74) *Attorney, Agent, or Firm* — Patrick Y. Ikehara

(57) ABSTRACT

A surgical access device has a surgical retractor having a noncompliant outer ring with an annular axis, an inner ring, and a sleeve coupling the outer ring to the inner ring. The noncompliant outer ring is adapted to roll over itself around the annular axis to roll the sleeve around the outer ring to retract and seal an opening in a biological body wall. The access device may include a lid adapted for being coupled to the noncompliant outer ring of the surgical retractor. The outer ring of the surgical retractor has a cross-sectional shape that prohibits the lid from being partially or incorrectly coupled to the outer ring of the surgical retractor.

30 Claims, 18 Drawing Sheets

(56) References Cited

U.S. PATENT DOCUMENTS

| | | |
|---|---|---|
| 1,598,284 A | 8/1926 | Kinney |
| 1,690,995 A | 11/1928 | Pratt |
| 1,180,466 A | 6/1931 | Deutsch |
| 1,810,466 A | 6/1931 | Deutsch |
| 2,219,564 A | 10/1940 | Reyniers |
| 2,305,289 A | 12/1942 | Coburg |
| 2,478,586 A | 8/1949 | Krapp |
| 2,669,991 A | 2/1954 | Curutchet |
| 2,695,608 A | 11/1954 | Gibbon |
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,057,350 A | 10/1962 | Cowley |
| 3,111,943 A | 11/1963 | Orndorff |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,717,883 A | 2/1973 | Mosher |
| 3,729,006 A | 4/1973 | Wilder et al. |
| 3,729,027 A * | 4/1973 | Bare .............................. 138/109 |
| 3,782,370 A | 1/1974 | McDonald |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds et al. |
| 3,841,332 A | 10/1974 | Treacle |
| 3,850,172 A | 11/1974 | Cazalis |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,082,005 A | 4/1978 | Erdley |
| 4,083,370 A | 4/1978 | Taylor |
| 4,096,853 A | 6/1978 | Weigand |
| 4,112,932 A | 9/1978 | Chiulli |
| 4,130,113 A | 12/1978 | Graham |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Banjamin |
| 4,306,562 A | 12/1981 | Osborne |
| 4,321,915 A | 3/1982 | Leighton et al. |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton |
| 4,691,942 A | 9/1987 | Ford |
| 4,714,749 A | 12/1987 | Hughes et al. |
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |
| 4,796,629 A | 1/1989 | Grayzel |
| 4,798,594 A | 1/1989 | Hillstead |
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |
| 4,848,575 A | 7/1989 | Nakamura et al. |
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |

(56) References Cited

U.S. PATENT DOCUMENTS

| | | |
|---|---|---|
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima et al. |
| 5,104,389 A | 4/1992 | Deem et al. |
| 5,125,396 A | 6/1992 | Ray |
| 5,125,897 A | 6/1992 | Quinn et al. |
| 5,127,626 A | 7/1992 | Hilal et al. |
| 5,129,885 A | 7/1992 | Green et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,167,637 A | 12/1992 | Okada et al. |
| 5,176,648 A | 1/1993 | Holmes et al. |
| 5,176,662 A | 1/1993 | Bartholomew et al. |
| 5,176,697 A | 1/1993 | Hasson et al. |
| 5,178,162 A | 1/1993 | Bose |
| 5,180,365 A | 1/1993 | Ensminger et al. |
| 5,183,471 A | 2/1993 | Wilk |
| 5,188,595 A | 2/1993 | Jacobi |
| 5,188,607 A | 2/1993 | Wu |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Rirchart et al. |
| 5,211,370 A | 5/1993 | Powers |
| 5,211,633 A | 5/1993 | Stouder, Jr. |
| 5,213,114 A | 5/1993 | Bailey, Jr. |
| 5,226,890 A | 7/1993 | Ianniruberto et al. |
| 5,234,455 A | 8/1993 | Mulhollan |
| 5,241,968 A | 9/1993 | Slater |
| 5,242,409 A | 9/1993 | Buelna |
| 5,242,412 A | 9/1993 | Blake, III |
| 5,242,415 A | 9/1993 | Kantrowitz et al. |
| 5,242,459 A | 9/1993 | Buelna |
| 5,248,304 A | 9/1993 | Vigdorchik et al. |
| 5,256,150 A | 10/1993 | Quiachon et al. |
| 5,257,973 A | 11/1993 | Villasuso |
| 5,257,975 A | 11/1993 | Foshee |
| 5,259,366 A | 11/1993 | Reydel et al. |
| 5,261,883 A | 11/1993 | Hood et al. |
| 5,262,468 A | 11/1993 | Chen |
| 5,263,922 A | 11/1993 | Sova et al. |
| 5,269,763 A | 12/1993 | Boehmer et al. |
| 5,269,772 A | 12/1993 | Wilk |
| 5,273,449 A | 12/1993 | Mattis et al. |
| 5,273,545 A | 12/1993 | Hunt et al. |
| D343,236 S | 1/1994 | Quigley et al. |
| 5,279,575 A | 1/1994 | Sugarbaker |
| 5,290,310 A | 3/1994 | Makower et al. |
| D346,022 S | 4/1994 | Quigley et al. |
| 5,299,582 A | 4/1994 | Potts |
| 5,300,034 A | 4/1994 | Behnke |
| 5,300,035 A | 4/1994 | Clement |
| 5,300,036 A | 4/1994 | Mueller et al. |
| 5,308,336 A | 5/1994 | Hart et al. |
| 5,309,896 A | 5/1994 | Moll et al. |
| 5,312,391 A | 5/1994 | Wilk |
| 5,314,417 A | 5/1994 | Stephens et al. |
| 5,316,541 A | 5/1994 | Fischer |
| 5,320,611 A | 6/1994 | Bonutti et al. |
| 5,330,437 A | 7/1994 | Durman |
| 5,330,486 A | 7/1994 | Wilk |
| 5,330,497 A | 7/1994 | Freitas et al. |
| 5,331,975 A | 7/1994 | Bonutti |
| 5,334,143 A | 8/1994 | Carroll |
| 5,336,192 A | 8/1994 | Palestrant |
| 5,336,708 A | 8/1994 | Chen |
| 5,338,313 A | 8/1994 | Mollenauer et al. |
| 5,342,315 A | 8/1994 | Rowe et al. |
| 5,342,385 A | 8/1994 | Norelli et al. |
| 5,350,364 A | 9/1994 | Stephens et al. |
| 5,353,786 A | 10/1994 | Wilk |
| 5,354,280 A | 10/1994 | Haber et al. |
| 5,360,417 A | 11/1994 | Gravener et al. |
| 5,364,345 A | 11/1994 | Lowery et al. |
| 5,364,372 A | 11/1994 | Danks et al. |
| 5,366,446 A | 11/1994 | Tal et al. |
| 5,366,478 A | 11/1994 | Brinkerhoff et al. |
| 5,368,545 A | 11/1994 | Schaller et al. |
| 5,375,588 A | 12/1994 | Yoon |
| 5,380,288 A | 1/1995 | Hart et al. |
| 5,383,861 A | 1/1995 | Hempel et al. |
| 5,385,552 A | 1/1995 | Haber et al. |
| 5,385,553 A | 1/1995 | Hart et al. |
| 5,385,560 A | 1/1995 | Wulf |
| 5,389,080 A | 2/1995 | Yoon |
| 5,389,081 A | 2/1995 | Castro |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers et al. |
| 5,403,336 A | 4/1995 | Kieturakis et al. |
| 5,407,433 A | 4/1995 | Loomas |
| 5,411,483 A | 5/1995 | Loomas |
| 5,413,571 A | 5/1995 | Katsaros et al. |
| 5,423,848 A | 6/1995 | Washizuka et al. |
| 5,429,609 A | 7/1995 | Yoon |
| 5,431,676 A | 7/1995 | Durdal et al. |
| 5,437,683 A | 8/1995 | Neumann et al. |
| 5,439,455 A | 8/1995 | Kieturakis et al. |
| 5,441,486 A | 8/1995 | Yoon |
| 5,443,452 A | 8/1995 | Hart et al. |
| 5,456,284 A | 10/1995 | Ryan et al. |
| 5,460,170 A | 10/1995 | Hammerslag |
| 5,460,616 A | 10/1995 | Weinstein et al. |
| 5,468,248 A | 11/1995 | Chin et al. |
| 5,476,475 A | 12/1995 | Gadberry |
| 5,480,410 A | 1/1996 | Cuschieri et al. |
| 5,486,426 A | 1/1996 | McGee et al. |
| 5,490,843 A | 2/1996 | Hildwein et al. |
| 5,492,304 A | 2/1996 | Smith et al. |
| 5,496,280 A | 3/1996 | Vandenbroek et al. |
| 5,503,112 A | 4/1996 | Luhman et al. |
| 5,507,758 A | 4/1996 | Thomason et al. |
| 5,508,334 A | 4/1996 | Chen |
| 5,511,564 A | 4/1996 | Wilk |
| 5,514,109 A | 5/1996 | Mollenauer et al. |
| 5,514,133 A | 5/1996 | Golub et al. |
| 5,514,153 A | 5/1996 | Bonutti |
| 5,518,278 A | 5/1996 | Sampson |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,531,758 A | 7/1996 | Uschold et al. |
| 5,538,509 A | 7/1996 | Dunlap et al. |
| 5,540,648 A | 7/1996 | Yoon |
| 5,540,711 A | 7/1996 | Kieturakis et al. |
| 5,545,150 A | 8/1996 | Danks et al. |
| 5,545,179 A | 8/1996 | Williamson, IV |
| 5,549,563 A | 8/1996 | Kronner |
| 5,549,637 A | 8/1996 | Crainich |
| 5,554,124 A | 9/1996 | Alvarado |
| 5,562,632 A | 10/1996 | Davila et al. |
| 5,562,677 A | 10/1996 | Hildwein et al. |
| 5,562,688 A | 10/1996 | Riza |
| 5,571,115 A | 11/1996 | Nicholas |
| 5,571,137 A | 11/1996 | Marlow et al. |
| 5,575,799 A | 11/1996 | Bolanos et al. |
| 5,577,993 A | 11/1996 | Zhu et al. |
| 5,578,048 A | 11/1996 | Pasqualucci et al. |
| 5,580,344 A | 12/1996 | Hasson |
| 5,584,850 A | 12/1996 | Hart et al. |
| 5,601,579 A | 2/1997 | Semertzides |

(56) References Cited

U.S. PATENT DOCUMENTS

| | | |
|---|---|---|
| 5,601,581 A | 2/1997 | Fogarty et al. |
| 5,603,702 A | 2/1997 | Smith et al. |
| 5,607,443 A | 3/1997 | Kieturakis et al. |
| 5,620,415 A | 4/1997 | Lucey et al. |
| 5,620,420 A | 4/1997 | Kriesel |
| 5,628,732 A | 5/1997 | Antoon, Jr. et al. |
| 5,632,284 A | 5/1997 | Graether |
| 5,632,979 A | 5/1997 | Goldberg et al. |
| 5,634,911 A | 6/1997 | Hermann et al. |
| 5,634,936 A | 6/1997 | Linden et al. |
| 5,634,937 A | 6/1997 | Mollenauer et al. |
| 5,636,645 A | 6/1997 | Ou |
| 5,640,977 A | 6/1997 | Leahy et al. |
| 5,643,301 A | 7/1997 | Mollenauer |
| 5,649,550 A | 7/1997 | Crook |
| 5,651,771 A | 7/1997 | Tangherlini et al. |
| 5,653,705 A | 8/1997 | de la Torre et al. |
| 5,657,963 A | 8/1997 | Hinchliffe et al. |
| 5,658,272 A | 8/1997 | Hasson |
| 5,658,306 A | 8/1997 | Kieturakis |
| 5,662,615 A | 9/1997 | Blake, III |
| 5,672,168 A | 9/1997 | de la Torre et al. |
| 5,681,341 A | 10/1997 | Lunsford et al. |
| 5,683,378 A | 11/1997 | Christy |
| 5,685,854 A | 11/1997 | Green et al. |
| 5,685,857 A | 11/1997 | Negus et al. |
| 5,697,914 A | 12/1997 | Brimhall |
| 5,707,703 A | 1/1998 | Rothrum et al. |
| 5,709,664 A | 1/1998 | Vandenbroek et al. |
| 5,713,858 A | 2/1998 | Heruth et al. |
| 5,713,869 A | 2/1998 | Morejon |
| 5,720,730 A | 2/1998 | Blake, III |
| 5,725,536 A | 3/1998 | Oberlin et al. |
| 5,728,103 A | 3/1998 | Picha et al. |
| 5,730,748 A | 3/1998 | Fogarty et al. |
| 5,735,791 A | 4/1998 | Alexander et al. |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,755,660 A | 5/1998 | Tyagi |
| 5,760,117 A | 6/1998 | Chen |
| 5,769,783 A | 6/1998 | Fowler |
| 5,782,812 A | 7/1998 | Hart et al. |
| 5,782,817 A | 7/1998 | Franzel et al. |
| 5,782,859 A | 7/1998 | Nicholas et al. |
| 5,788,676 A | 8/1998 | Yoon |
| 5,792,119 A | 8/1998 | Marx |
| 5,795,290 A | 8/1998 | Bridges |
| 5,803,919 A | 9/1998 | Hart et al. |
| 5,803,921 A | 9/1998 | Bonadio |
| 5,803,923 A | 9/1998 | Singh-Derewa et al. |
| 5,807,350 A | 9/1998 | Diaz |
| 5,810,712 A | 9/1998 | Dunn |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom et al. |
| 5,819,375 A | 10/1998 | Kastner |
| 5,820,555 A | 10/1998 | Watkins, III et al. |
| 5,820,600 A | 10/1998 | Carlson et al. |
| 5,830,191 A | 11/1998 | Hildwein et al. |
| 5,832,925 A | 11/1998 | Rothrum |
| 5,836,871 A | 11/1998 | Wallace et al. |
| 5,841,298 A | 11/1998 | Huang |
| 5,842,971 A | 12/1998 | Yoon |
| 5,848,992 A | 12/1998 | Hart et al. |
| 5,853,395 A | 12/1998 | Crook et al. |
| 5,853,417 A | 12/1998 | Fogarty et al. |
| 5,857,461 A | 1/1999 | Levitsky et al. |
| 5,860,995 A | 1/1999 | Berkelaar |
| 5,865,728 A | 2/1999 | Moll et al. |
| 5,865,729 A | 2/1999 | Meehan et al. |
| 5,865,807 A | 2/1999 | Blake, III |
| 5,865,817 A | 2/1999 | Moenning et al. |
| 5,871,474 A | 2/1999 | Hermann et al. |
| 5,876,413 A | 3/1999 | Fogarty et al. |
| 5,879,368 A | 3/1999 | Hoskin et al. |
| 5,882,344 A | 3/1999 | Stouder, Jr. |
| 5,884,639 A | 3/1999 | Chen |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,913,847 A | 6/1999 | Yoon |
| 5,916,198 A | 6/1999 | Dillow |
| 5,916,232 A | 6/1999 | Hart |
| 5,919,476 A | 7/1999 | Fischer et al. |
| 5,931,832 A | 8/1999 | Jensen |
| 5,947,922 A | 9/1999 | MacLeod |
| 5,951,467 A | 9/1999 | Picha et al. |
| 5,951,588 A | 9/1999 | Moenning |
| 5,957,888 A | 9/1999 | Hinchliffe, et al. |
| 5,957,913 A | 9/1999 | de la Torre et al. |
| 5,962,572 A | 10/1999 | Chen |
| 5,964,781 A | 10/1999 | Mollenauer et al. |
| 5,976,174 A | 11/1999 | Ruiz |
| 5,989,232 A | 11/1999 | Yoon |
| 5,989,233 A | 11/1999 | Yoon |
| 5,989,266 A | 11/1999 | Foster |
| 5,993,471 A | 11/1999 | Riza et al. |
| 5,993,485 A | 11/1999 | Beckers |
| 5,994,450 A | 11/1999 | Pearce |
| 5,997,515 A | 12/1999 | de la Torre et al. |
| 6,004,303 A | 12/1999 | Peterson |
| 6,010,494 A | 1/2000 | Schafer et al. |
| 6,017,355 A | 1/2000 | Hessel et al. |
| 6,018,094 A | 1/2000 | Fox |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,035,559 A | 3/2000 | Freed et al. |
| 6,042,573 A | 3/2000 | Lucey |
| 6,045,535 A | 4/2000 | Ben Nun |
| 6,048,309 A | 4/2000 | Flom et al. |
| 6,050,871 A | 4/2000 | Chen |
| 6,053,934 A | 4/2000 | Andrews et al. |
| 6,059,806 A | 5/2000 | Hoegerle |
| 6,066,117 A | 5/2000 | Fox et al. |
| 6,068,639 A | 5/2000 | Fogarty et al. |
| 6,076,560 A * | 6/2000 | Stahle et al. ............... 138/112 |
| 6,077,288 A | 6/2000 | Shimomura |
| 6,086,603 A | 7/2000 | Termin et al. |
| 6,090,043 A | 7/2000 | Austin et al. |
| 6,099,506 A | 8/2000 | Macoviak et al. |
| 6,110,154 A | 8/2000 | Shimomura et al. |
| 6,123,689 A | 9/2000 | To |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,197,002 B1 | 3/2001 | Peterson |
| 6,217,555 B1 | 4/2001 | Hart et al. |
| 6,217,590 B1 | 4/2001 | Levinson |
| 6,224,612 B1 | 5/2001 | Bates et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,533 B1 | 7/2001 | Fadem et al. |
| 6,254,534 B1 | 7/2001 | Butler et al. |
| 6,258,065 B1 | 7/2001 | Dennis et al. |
| 6,264,604 B1 | 7/2001 | Kieturakis et al. |

(56) References Cited

U.S. PATENT DOCUMENTS

| | | |
|---|---|---|
| 6,267,751 B1 | 7/2001 | Mangosong |
| 6,276,661 B1 | 8/2001 | Laird |
| 6,287,280 B1 | 9/2001 | Lampropoulos et al. |
| 6,315,770 B1 | 11/2001 | de la Torre et al. |
| 6,319,246 B1 | 11/2001 | de la Torre et al. |
| 6,322,541 B2 | 11/2001 | West |
| 6,325,384 B1 | 12/2001 | Berry, Sr. et al. |
| 6,346,074 B1 | 2/2002 | Roth |
| 6,371,968 B1 | 4/2002 | Kogasaka et al. |
| 6,382,211 B1 | 5/2002 | Crook |
| 6,383,162 B1 | 5/2002 | Sugarbaker |
| 6,391,043 B1 | 5/2002 | Moll et al. |
| 6,413,244 B1 | 7/2002 | Bestetti et al. |
| 6,413,458 B1 | 7/2002 | Pearce |
| 6,420,475 B1 | 7/2002 | Chen |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 | 4/2003 | Bimbo et al. |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,569,120 B1 | 5/2003 | Green |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo et al. |
| 6,669,674 B1 | 12/2003 | Macoviak et al. |
| 6,676,639 B1 | 1/2004 | Ternström |
| 6,702,787 B2 | 3/2004 | Racenet et al. |
| 6,705,989 B2 | 3/2004 | Cuschieri et al. |
| 6,706,050 B1 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B1 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,037 B2 | 8/2005 | Bubb et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Lui et al. |
| 7,105,009 B2 | 9/2006 | Johnson |
| 7,105,607 B2 | 9/2006 | Chen |
| 7,112,185 B2 | 9/2006 | Hart et al. |
| 7,118,528 B1 | 10/2006 | Piskun |
| 7,134,929 B2 | 11/2006 | Chen |
| 7,153,261 B2 | 12/2006 | Wenchell |
| 7,163,510 B2 | 1/2007 | Kahle et al. |
| 7,192,436 B2 | 3/2007 | Sing et al. |
| 7,193,002 B2 | 3/2007 | Chen |
| 7,195,590 B2 | 3/2007 | Butler et al. |
| 7,214,185 B1 | 5/2007 | Rosney et al. |
| 7,217,277 B2 | 5/2007 | Parihar et al. |
| 7,222,380 B2 | 5/2007 | Chen |
| 7,223,257 B2 | 5/2007 | Shubayev et al. |
| 7,223,278 B2 | 5/2007 | Davison et al. |
| 7,226,484 B2 | 6/2007 | Chen |
| 7,235,062 B2 | 6/2007 | Brustad |
| 7,235,084 B2 | 6/2007 | Skakoon et al. |
| 7,238,154 B2 | 7/2007 | Ewers et al. |
| 7,244,244 B2 | 7/2007 | Racenet et al. |
| 7,276,075 B1 | 10/2007 | Callas et al. |
| 7,290,367 B2 | 11/2007 | Chen |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,338,473 B2 | 3/2008 | Campbell et al. |
| 7,344,546 B2 | 3/2008 | Wulfman et al. |
| 7,344,547 B2 | 3/2008 | Piskun |
| 7,344,568 B2 | 3/2008 | Chen |
| 7,377,898 B2 | 5/2008 | Ewers et al. |
| 7,390,317 B2 | 6/2008 | Taylor et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,578,832 B2 | 8/2009 | Johnson |

(56) References Cited

U.S. PATENT DOCUMENTS

| | | |
|---|---|---|
| 7,645,232 B2 | 1/2010 | Shluzas |
| 7,650,887 B2 | 1/2010 | Nguyen et al. |
| 7,661,164 B2 | 2/2010 | Chen |
| 7,704,207 B2 | 4/2010 | Albrecht et al. |
| 7,717,847 B2 | 5/2010 | Smith |
| 7,727,146 B2 | 6/2010 | Albrecht et al. |
| 7,727,255 B2 | 6/2010 | Taylor et al. |
| 7,736,306 B2 | 6/2010 | Brustad et al. |
| 7,749,415 B2 | 7/2010 | Brustad et al. |
| 7,753,901 B2 | 7/2010 | Piskun et al. |
| 7,758,500 B2 | 7/2010 | Boyd et al. |
| 7,766,824 B2 | 8/2010 | Jensen et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,841,765 B2 * | 11/2010 | Keller .................... 366/339 |
| 7,850,667 B2 | 12/2010 | Gresham |
| 7,867,164 B2 | 1/2011 | Butler et al. |
| 7,878,974 B2 | 2/2011 | Brustad et al. |
| 7,883,461 B2 | 2/2011 | Albrecht et al. |
| 7,892,172 B2 | 2/2011 | Albrecht et al. |
| 7,896,889 B2 | 3/2011 | Mazzocchi et al. |
| 7,909,760 B2 | 3/2011 | Albrecht et al. |
| 7,913,697 B2 | 3/2011 | Nguyen et al. |
| 7,930,782 B2 | 4/2011 | Chen |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0026230 A1 | 2/2002 | Moll et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0004253 A1 | 1/2003 | Chen |
| 2003/0014076 A1 | 1/2003 | Mollenauer et al. |
| 2003/0028179 A1 | 2/2003 | Piskun |
| 2003/0040711 A1 | 2/2003 | Racenet et al. |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0267096 A1 | 12/2004 | Caldwell et al. |
| 2005/0020884 A1 | 1/2005 | Hart et al. |
| 2005/0033246 A1 | 2/2005 | Ahlberg et al. |
| 2005/0059865 A1 * | 3/2005 | Kahle et al. .................... 600/206 |
| 2005/0065475 A1 | 3/2005 | Hart et al. |
| 2005/0065543 A1 | 3/2005 | Kahle et al. |
| 2005/0080319 A1 * | 4/2005 | Dinkler, II et al. .............. 600/201 |
| 2005/0090713 A1 | 4/2005 | Gonzales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0251124 A1 | 11/2005 | Zvuloni et al. |
| 2005/0257355 A1 * | 11/2005 | Provenzale .................... 24/715.4 |
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0052669 A1 | 3/2006 | Hart |
| 2006/0084842 A1 | 4/2006 | Hart et al. |
| 2006/0106402 A1 | 5/2006 | McLucas |
| 2006/0129165 A1 | 6/2006 | Edoga et al. |
| 2006/0149137 A1 * | 7/2006 | Pingleton et al. .............. 600/208 |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0168785 A1 * | 8/2006 | Kraft et al. .................... 24/715.3 |
| 2006/0241651 A1 | 10/2006 | Wilk |
| 2006/0247498 A1 * | 11/2006 | Bonadio et al. ................ 600/208 |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0088202 A1 * | 4/2007 | Albrecht et al. .............. 600/201 |
| 2007/0088204 A1 | 4/2007 | Albrecht |
| 2007/0093695 A1 | 4/2007 | Bonadio et al. |
| 2007/0118175 A1 | 5/2007 | Butler et al. |
| 2007/0149859 A1 | 6/2007 | Albrecht et al. |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0200767 A1 | 8/2008 | Ewers et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |

(56) References Cited

U.S. PATENT DOCUMENTS

| | | |
|---|---|---|
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0187079 A1 | 7/2009 | Albrecht et al. |
| 2009/0227843 A1 | 9/2009 | Smith et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0081995 A1 | 4/2010 | Widenhouse et al. |
| 2010/0100043 A1 | 4/2010 | Racenet |
| 2010/0113882 A1 | 5/2010 | Widenhouse et al. |
| 2010/0217087 A1 | 8/2010 | Bonadio et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249523 A1 | 9/2010 | Spiegal et al. |
| 2010/0249524 A1 | 9/2010 | Ransden et al. |
| 2010/0249525 A1 | 9/2010 | Shelton, IV et al. |
| 2010/0249694 A1 | 9/2010 | Choi et al. |
| 2010/0261972 A1 | 10/2010 | Widenhouse et al. |
| 2010/0261975 A1 | 10/2010 | Huey et al. |
| 2010/0286484 A1 | 11/2010 | Stellon et al. |
| 2010/0298646 A1 | 11/2010 | Stellon et al. |
| 2011/0021877 A1 | 1/2011 | Fortier et al. |
| 2011/0028891 A1 | 2/2011 | Okoniewski |
| 2011/0034935 A1 | 2/2011 | Kleyman |
| 2011/0034946 A1 | 2/2011 | Kleyman |
| 2011/0034947 A1 | 2/2011 | Kleyman |
| 2011/0071462 A1 | 3/2011 | Ewers et al. |
| 2011/0071463 A1 | 3/2011 | Ewers et al. |

FOREIGN PATENT DOCUMENTS

| | | |
|---|---|---|
| DE | 37 39 532 | 12/1988 |
| DE | 37 37 121 | 5/1989 |
| DE | 296 00 939 | 6/1996 |
| DE | 19828009 | 12/1999 |
| EP | 0113520 | 7/1984 |
| EP | 0142262 | 5/1985 |
| EP | 0 517 248 | 12/1992 |
| EP | 0537768 | 4/1993 |
| EP | 0 807 416 | 11/1997 |
| EP | 0 849 517 | 6/1998 |
| EP | 0950376 | 10/1999 |
| EP | 1118657 | 7/2001 |
| EP | 1 125 552 | 8/2001 |
| EP | 1312318 | 5/2003 |
| EP | 1 407 715 | 4/2004 |
| EP | 2044889 | 4/2009 |
| EP | 2 340 792 | 7/2011 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |
| JP | 2002-28163 | 1/2002 |
| JP | 02003 235879 A | 8/2003 |
| JP | 2004-195037 | 7/2004 |
| SU | 1342485 | 1/1997 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/11642 | 4/1997 |
| WO | WO 97/32514 | 9/1997 |
| WO | WO 97/32515 | 9/1997 |
| WO | WO 97/42889 | 11/1997 |
| WO | WO 98/19853 | 5/1998 |
| WO | WO 98/35614 | 8/1998 |
| WO | WO 98/48724 | 11/1998 |
| WO | WO 99/03416 | 1/1999 |
| WO | WO 99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO 00/32116 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/26559 | 4/2001 |
| WO | WO 01/45568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO 02/34108 | 5/2002 |
| WO | WO 03/011153 | 2/2003 |
| WO | WO 03/011551 | 2/2003 |
| WO | WO 03/026512 | 4/2003 |
| WO | WO 03/032819 | 4/2003 |
| WO | WO 03/034908 | 5/2003 |
| WO | WO 03/061480 | 7/2003 |
| WO | WO 03/077726 | 9/2003 |
| WO | WO 03/103548 | 12/2003 |
| WO | WO 2004/026153 | 4/2004 |
| WO | WO 2004/030547 | 4/2004 |
| WO | WO 2004/075730 | 9/2004 |
| WO | WO 2004/075741 | 9/2004 |

(56) References Cited

FOREIGN PATENT DOCUMENTS

| WO | WO 2004/075930 | 9/2004 |
|---|---|---|
| WO | WO 2005/009257 | 2/2005 |
| WO | WO 2005/034766 | 4/2005 |
| WO | WO 2005/089661 | 9/2005 |
| WO | WO 2006/040748 | 4/2006 |
| WO | WO 2006/059318 | 6/2006 |
| WO | WO 2006/100658 | 9/2006 |
| WO | WO 2007/044849 | 4/2007 |
| WO | WO 2008/015566 | 2/2008 |
| WO | WO 2008/093313 | 8/2008 |
| WO | WO 2008/121294 | 10/2008 |
| WO | WO 2010/082722 | 7/2010 |
| WO | WO 2010/104259 | 9/2010 |

OTHER PUBLICATIONS

US 5,334,646, Chen, (withdrawn).
U.S. Appl. No. 10/902,756, filed Jul. 29, 2004; Title: Hand Access Port Device, now abandoned.
U.S. Appl. No. 10/802,125, filed Mar. 15, 2004; Title: Surgical Guide Valve, now abandoned.
U.S. Appl. No. 10/927,551, filed Aug. 25, 2004; Title: Surgical Access System, now abandoned.
U.S. Appl. No. 10/695,295, filed Oct. 28, 2003; Title: Surgical Gel Seal.
U.S. Appl. No. 11/132,741, filed May 18, 2005; Title: Gas-Tight Seal Accomodating Surgical Instruments With a Wide Range of Diameters.
U.S. Appl. No. 11/245,709, filed Oct. 7, 2005; Title: Surgical Access System.
U.S. Appl. No. 11/330,661, filed Jan. 12, 2006; Title: Sealed Surgical Access Device.
U.S. Appl. No. 11/564,409, filed Nov. 29, 2006; Title: Surgical Instrument Access Device.
U.S. Appl. No. 12/108,400, filed Apr. 23, 2008; Title: Wound Retraction Apparatus and Method.
U.S. Appl. No. 12/119,371, filed May 12, 2008; Title: Surgical Retractor With Gel Pad.
U.S. Appl. No. 12/119,414, filed May 12, 2008; Title: Surgical Retractor.
U.S. Appl. No. 12/358,080, filed Jan. 22, 2009; Title: Surgical Instrument Access Device.
U.S. Appl. No. 12/360,634, filed Jan. 27, 2009; Title: Surgical Access Apparatus and Method.
U.S. Appl. No. 12/360,710, filed Jan. 27, 2009; Title: Surgical Access Apparatus and Method.
U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011.
U.S. Appl. No. 13/008,728, filed Jan. 18, 2011.
U.S. Appl. No. 13/023,334, filed Feb. 8, 2011.
U.S. Appl. No. 13/031,892, filed Feb. 22, 2011.
U.S. Appl. No. 13/050,042, filed Mar. 17, 2011.
U.S. Appl. No. 10/446,365, filed May 28, 2003; Title: Screw-Type Seal With Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal With Inflatable Membrane.
U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for Use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic Instrument and Cannula Assembly and Related Surgical Method.
U.S. Appl. No. 10/913,565, filed Aug. 5, 2004; Title: Surgical Device With Tack-Free Gel and Method of Manufacture.
Dexterity Protractor Instruction Manual by Dexterity Surgical, Inc.
European Patent Office, European Search Report for European Application No. EP 10 18 4681, dated Nov. 22, 2010, entitled "Wound Retraction Apparatus and Method".
European Patent Office, European Search Report for European Application No. EP 10 18 4608, dated Nov. 22, 2010, entitled "Wound Retraction Apparatus and Method".
European Patent Office, European Search Report for European Application No. EP 10 18 4648, dated Nov. 22, 2010, entitled "Wound Retraction Apparatus and Method".
European Patent Office, European Search Report for European Application No. EP 10 18 4731, dated Nov. 22, 2010, entitled "Wound Retraction Apparatus and Method".
European Patent Office, European Search Report for European Application No. EP 10 18 4661, dated Nov. 22, 2010, entitled "Wound Retraction Apparatus and Method".
European Patent Office, European Search Report for European Application No. EP 10 18 4677, dated Nov. 22, 2010, entitled "Wound Retraction Apparatus and Method".
European Patent Office, European Search Report for European Application No. EP 10 18 9325, dated Dec. 14, 2010, entitled "Split Hoop Wound Retractor".
European Patent Office, European Search Report for European Application No. EP 10 18 9327, dated Dec. 14, 2010, entitled "Split Hoop Wound Retractor".
European Patent Office, European Search Report for European Application No. EP 10 18 9328, dated Dec. 15, 2010, entitled "Split Hoop Wound Retractor".
European Patent Office, European Search Report for European Application No. EP 04 00 2888, dated Sep. 10, 2004, entitled "Hand Access Port Device".
European Patent Office, European Search Report for European Application No. EP 04 00 2889, dated Sep. 13, 2004, entitled "Hand Access Port Device".
European Patent Office, International Search Report and the Written Opinion of the International Searching Authority for International Application No. PCT/US2006/040154, mailed Jan. 30, 2007.
European Patent Office, International Search Report and the Written Opinion of the International Searching Authority for International Application No. PCT/US2006/040073, mailed Jan. 26, 2007.
European Patent Office, International Search Report and the Written Opinion of the International Searching Authority for International Application No. PCT/US2006/039905, mailed Jan. 17, 2007.
European Patent Office, International Search Report and the Written Opinion of the International Searching Authority for International Application No. PCT/US2006/039883, mailed Jan. 31, 2007.
European Patent Office, International Search Report and the Written Opinion of the International Searching Authority for International Application No. PCT/US2006/039800, mailed Apr. 16, 2007.
European Patent Office, International Search Report and the Written Opinion of the International Searching Authority for International Application No. PCT/US2006/039799, mailed Mar. 27, 2007.

(56) References Cited

OTHER PUBLICATIONS

European Search Report for corresponding EP 08253236 date of mailing is Feb. 10, 2009 (6 pages).
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484.
International Searching Authority/US, International Search Report and the Written Opinion of the International Searching Authority for International Application No. PCT/US01/29682.
McSweeney, Cannulation of the Rumen in Cattle and Buffaloes, Australian Veterniary Journal, Aug. 1989, vol. 66, No. 8, pp. 266-268.
Neil Sheehan, Supplemental Expert Report of Neil Sheehan, Re: U.S. Patent No. 5,741,298, United States District Court for the Central District of California, Civil Action No. SACV 03-1322 JVS, Aug. 9, 2005.
Office Action in co-pending U.S. Appl. No. 12/360,634, dated Jan. 24, 2011 in 12 pages.
Office Action in co-pending U.S. Appl. No. 12/360,710, dated Jan. 24, 2011 in 12 pages.
Technical Note: Development of Duodenal Cannula for Sheep, Faculty of Agriculture and School of Medicine Tohokju University, Sendai 981, Japan.
The International Bureau of WIPO, International Preliminary Report on Patentability, dated Aug. 29, 2006, for International Application No. PCT/US2004/028250.
The International Bureau of WIPO, International Preliminary Report on Patentability, dated Apr. 16, 2008, for International Application No. PCT/US2006/039799.
The International Bureau of WIPO, International Preliminary Report on Patentability for International Application No. PCT/US2006/039800 dated Apr. 16, 2008.
Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.
Kagaya, Laparascopic cholecystecomy via two ports, using the "Twin-Port" system, J. Hepatobiliary Pancreat Surg (2001) 8:76-80.
International Search Report and Written Opinion in PCT/IE2005/000113 mailed on Feb. 22, 2006.
International Search Report and Written Opinion in PCT/IE2007/000050 mailed on Aug. 13, 2007.
Declaration of John R. Brustad dated Dec. 10, 2009, submitted in U.S. Appl. No. 11/548,955, including Appendices A-D regarding product sales brochures and production drawings from 2001 and 2005.
The International Searching Authority, The International Search Report and Written Opinion of the International Searching Authority for International Application No. PCT/US08/63445, mailed Sep. 29, 2008.
The International Searching Authority, The International Search Report and Written Opinion of the International Searching Authority for International Application No. PCT/US08/063463 mailed Sep. 10, 2008.
The International Bureau of WIPO, International Preliminary Report on Patentability for International Application No. PCT/US2008/063463, dated Nov. 17, 2009, entitled "Surgical Retractor".
International Searching Authority—US, International Search Report and Written Opinion of the International Searching Authority for International Application No. PCT/US04/25511, mailed Nov. 7, 2007.
International Bureau of WIPO, International Report on Patentability for International Application No. PCT/US04/25511, mailed Dec. 6, 2007.
The International Bureau of WIPO, International Preliminary Report on Patentability for International Application No. PCT/US08/63445, issued Nov. 17, 2009, entitled "Surgical Retractor with Gel Pad".
European Patent Office, European Search Report for European Patent No. 12151288, dated Feb. 10, 2012.
European Patent Office, Supplementary European Search Report for European Patent No. 08755322, dated Apr. 18, 2012.
European Patent Office, Supplementary European Search Report for European Patent No. 08755336, dated Jun. 6, 2012.
Harold W. Harrower, M.D., Isolation of Incisions into Body Cavities, The American Journal of Surgery, vol. 116, pp. 824-826, Dec. 1968.

\* cited by examiner

SURGICAL RETRACTOR WITH GEL PAD

CROSS-REFERENCE TO RELATED APPLICATIONS

This is a continuation of U.S. patent application No. 12/119,371, filed on May 12, 2008, now U.S. Pat. No. 8,109,873, issued Feb. 7, 2012, that claims the benefits of and priority to U.S. Provisional Patent Application No. 60/917,580, filed on May 11, 2007, the disclosures of which are hereby incorporated by reference as if set forth in full herein.

BACKGROUND

The present invention relates generally to surgical tissue retractors and specifically to retractors that may be used to enlarge a surgical incision or a natural body opening. Retraction of a surgical incision or body opening is generally accomplished by placing a first, flexible retention member through the incision or body opening and into a body cavity, such as an abdominal cavity, and subsequently tensioning the first retention member against the inner portion of the associated body wall adjacent to the incision or opening by applying tension to a sleeve that is coupled to the first tension member. The sleeve may be tensioned by winding it upon an external, more rigid structure. As the sleeve is wound around the external structure, the incision or opening is reshaped and/or enlarged to a substantially round condition.

SUMMARY

The invention relates generally to a surgical retractor for retracting a surgical incision or a natural biological body orifice. A surgical access device has a surgical retractor for retracting an opening in a biological body and a lid. The surgical retractor has a noncompliant outer ring, an inner ring, and a sleeve that couples the outer ring to the inner ring. The outer ring has an annular axis and is adapted for juxtaposition with an outer surface of the biological body wall. The inner ring is adapted for juxtaposition with an inner surface of the biological body wall. The sleeve is adapted to traverse the opening in the body wall. The noncompliant outer ring is adapted to roll over itself around the annular axis to roll the sleeve around the outer ring in order to retract and seal the opening in the body wall. The lid is adapted for being coupled to the noncompliant outer ring of the surgical retractor. The outer ring of the surgical retractor has a cross-sectional shape that prohibits the lid from being partially or incorrectly coupled to the outer ring of the surgical retractor.

In one aspect, the outer ring of the surgical retractor has an oval cross-sectional shape. The outer ring of the surgical retractor has a first, outer portion that has at least one lumen, and a second, inner portion that has a noncompliant hoop. The noncompliant hoop is positioned in the at least one lumen of the first, outer portion. In one aspect, the at least one lumen in the first, outer portion of the outer ring has a first, middle lumen, a second, top lumen, and a third, bottom lumen, with the noncompliant hoop of the second, inner portion of the outer ring being positioned in the first, middle lumen. The first, outer portion of the outer ring may have the oval cross-sectional shape with the first, second, and third lumens of the first, outer portion of the outer ring being positioned along a major axis of the oval cross-section. The first lumen is positioned at a minor axis of the oval cross-section, the second lumen is positioned on a first side of the minor axis and the third lumen is positioned on a second, opposite side of the minor axis. A split hoop may be positioned in each of the second and third lumens of the first, outer portion of the outer ring. In one aspect, the first, outer portion of the outer ring of the surgical retractor has two lumens with a noncompliant split hoop positioned in each of the two lumens of the first, outer portion of the outer ring of the surgical retractor. The first, outer portion of the outer ring is made of materials that allow the outer ring to be turned around its annular axis. The sleeve is made of a material that is flexible and impermeable to fluids and bacteria. The inner ring is made of materials having sufficient hardness to retain the shape of the inner ring after insertion of the inner ring into a body cavity. In one aspect, the lid is a gel cap that has a cap ring and a gel pad. The cap ring is adapted to be coupled to the outer ring of the surgical retractor. The gel pad is made of a gel material and is coupled to the cap ring. The gel pad of the gel cap may have an access portion for providing a passage from external the body to a body cavity. The passage forms an instrument seal in the presence of an instrument inserted therethrough and a zero seal in the absence of an instrument inserted therethrough. A distal portion of the cap ring may be adapted to receive the outer ring of the surgical retractor such that the outer ring of the surgical retractor embeds into the gel pad and displaces the gel, thereby forming a seal between the gel pad and the outer ring and sleeve of the surgical retractor.

These and other features and advantages of the invention will become more apparent with a discussion of embodiments in reference to the associated drawings.

DESCRIPTION

Figure 1A:
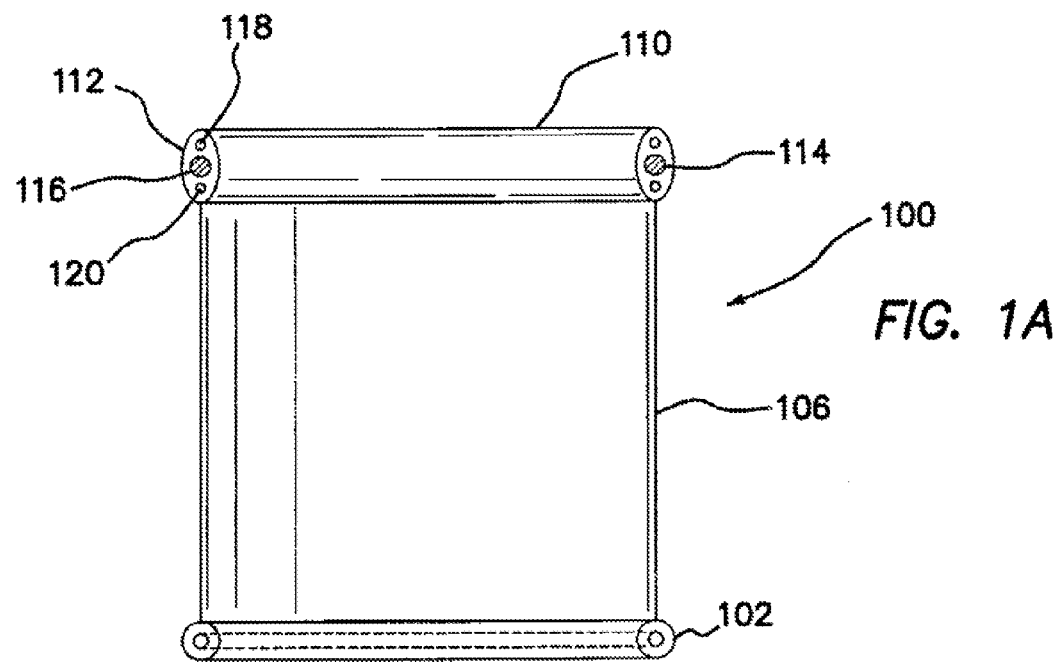
FIG. 1A is a side view of a surgical retractor in accordance with various aspects of the present invention.
Figure 1B:
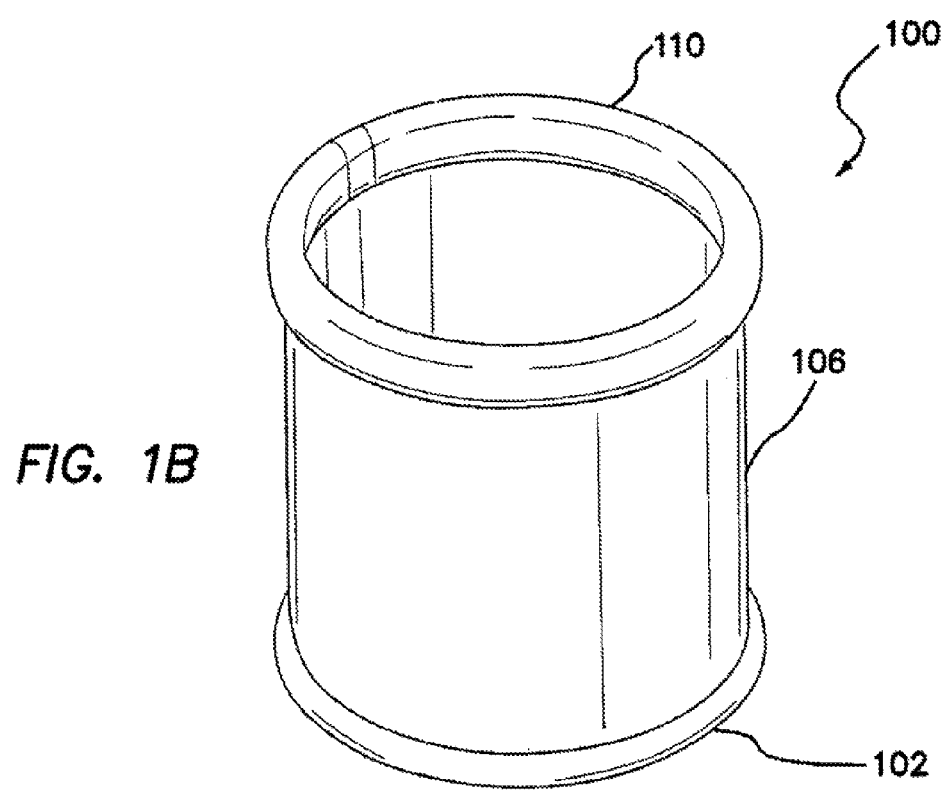
FIG. 1B is a perspective view of a surgical retractor in accordance with various aspects of the present invention.
Figure 2A:
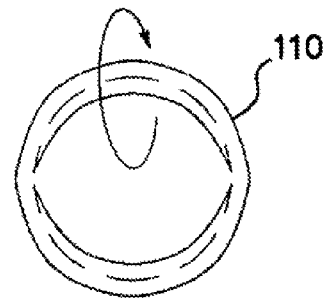
FIGS. 2A-2C are views of an outer ring of a surgical retractor in accordance with various aspects of the present invention.
Figure 2B:
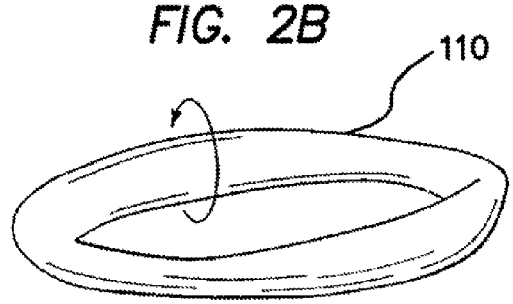
Figure 2C:
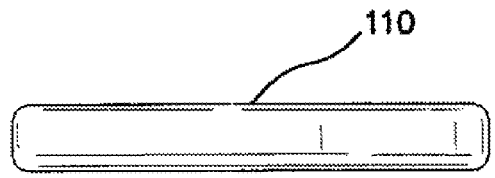

A surgical retractor 100 is placed into a surgical incision or body orifice to enlarge, reshape and isolate the incision or body orifice. Referring to FIGS. 1 and 2, the surgical retractor 100 includes a first, inner ring 102, a second, outer ring 110 and a sleeve 106 that couples the inner ring to the outer ring. The sleeve is flexible and may be substantially cylindrical. The first, inner ring 102 may be sufficiently flexible to be shaped into a compressed condition for insertion into the incision or body orifice and subsequently released within an associated body cavity where the inner ring substantially regains its original shape. In one aspect, the first, inner ring includes a substantially circular shape when it is released. The first, inner ring may be compressed to a substantially oval shape for insertion through the incision or body orifice. Those with ordinary skill in the art will recognize that the first, inner ring may include a shape other than round and that it may be compressed and reshaped to a shape other than oval. Once the first, inner ring is properly deployed within a body cavity, the connecting sleeve or film may be tensioned to some appropriate degree between the first, inner ring and the second, outer ring.

The second, outer ring 110 includes a first, outer component 112 and a second, inner component 114. The first, outer component 112 includes an overall shape that is substantially circular and may include a substantially oval cross-section. In one aspect, the height of the cross-section of the first, outer component 112 is larger than the width of the cross-section. Alternatively, the width of the cross-section of the first, outer component 112 is larger than the height of the cross-section. The ratio between the height and width of the cross-section relates to the hardness of the first, outer component 112 material and the diameter of the second, outer ring 110. More particularly, with a softer material for the first, outer component 112, the ratio between the height and width of the cross-section of the first, outer component is greater. Similarly, with the first, outer component 112 having a greater diameter, the ratio between the height and width of the cross-section of the first, outer component is greater. The first, outer component 112 may be made of a thermoplastic elastomeric material, such as a HYTREL, a thermoplastic polyester elastomeric material manufactured by E. I. DuPont de Nemours & Co. of Wilmington, Del., and/or PELLETHANE, a thermoplastic polyurethane elastomeric material manufactured by The Dow Chemical Company of Midland, Mich.

In one aspect, the first, outer component 112 of the second, outer ring 110 includes three lumens that extend throughout the outer component. A first, middle lumen 116 may include an oval cross-section and be sized larger than a second, top lumen 118 and a third, bottom lumen 120. The second, top lumen 118 and third, bottom lumen 120 may each include a tear-dropped cross-section having tapered portions away from the first, middle lumen 116. The first 116, second 118, and third 120 lumens are positioned substantially along a major axis of the oval cross-section of the outer component 112. The first lumen 116 is further positioned substantially at a minor axis of the oval cross-section of the outer component 112 of the outer ring 110, the second lumen 118 is positioned on a first side of the minor axis and the third lumen 120 is positioned on a second, opposite side of the minor axis. Alternatively, the cross-sectional shape of the first, outer component 112 may vary greatly from the oval shape. Further, the lumens may include other cross-sectional shapes, such as round. Alternatively, the first, outer component 112 of the outer ring 110 may include only a single lumen 116 extending throughout the first, outer component of the second, outer ring and positioned substantially in the center of the cross-section of the first, outer component of the second, outer ring. Additionally, the single lumen 116 in the first, outer component 112 of the second, outer ring 110 may be positioned off-center of the first, outer component.

The first, outer component 112 of the second, outer ring 110 may be made of a split piece of material, such as a substantially straight piece of material, having a first end 122 and a second end 124. The first 122 and second 124 ends of the material forming the first, outer component 112 may be brought proximate each other and coupled together, as will be discussed in more detail below.

In one aspect, the second, inner component 114 of the outer ring 110 is made of a rigid wire that is bent into a generally circular shape. The second, inner component 114 is inserted into the first, middle lumen 116 of the first, outer component 112. The wire is not compliant or resilient in relation to the body tissue of the surgical incision or natural body orifice. The wire does not flex, yield or deform in relation to the body tissue of the surgical incision or natural body orifice during retraction of the incision or body orifice. The rigid wire dictates the peripheral shape, or footprint, of the second, outer ring of the surgical retractor. The rigid wire marks the center point of rotation for the second, outer ring 110, thereby functioning as an axle about which the first, outer component 112 rotates. The wire may be made of full hard stainless steel, or other material that is significantly harder than the first, outer component 112 of the second, outer ring 110. The wire of which the second, inner component 114 is made may be a split wire having a first 126 end and a second end 128. In one aspect, the first 126 and second 128 ends of the rigid wire are coupled together.

Figure 3:
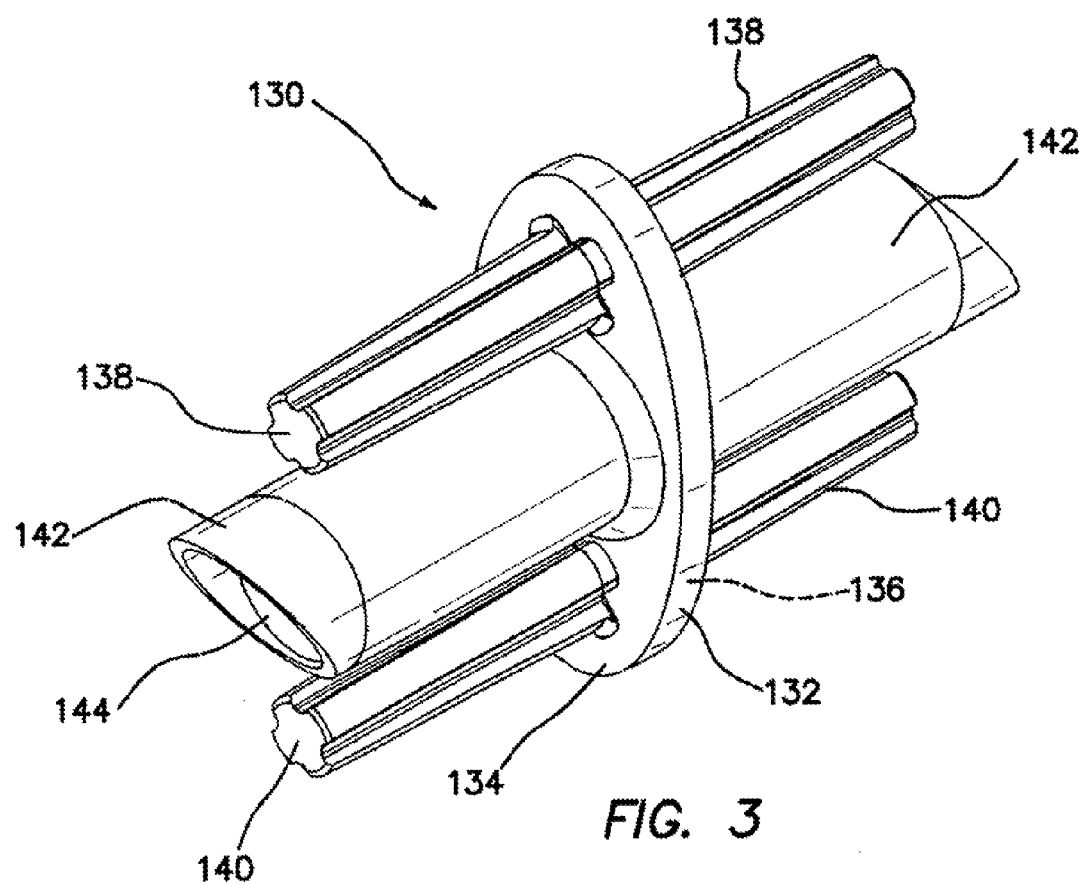
FIG. 3 is a perspective view of a coupler for the outer ring of the surgical retractor in accordance with various aspects of the present invention.
Figure 4:
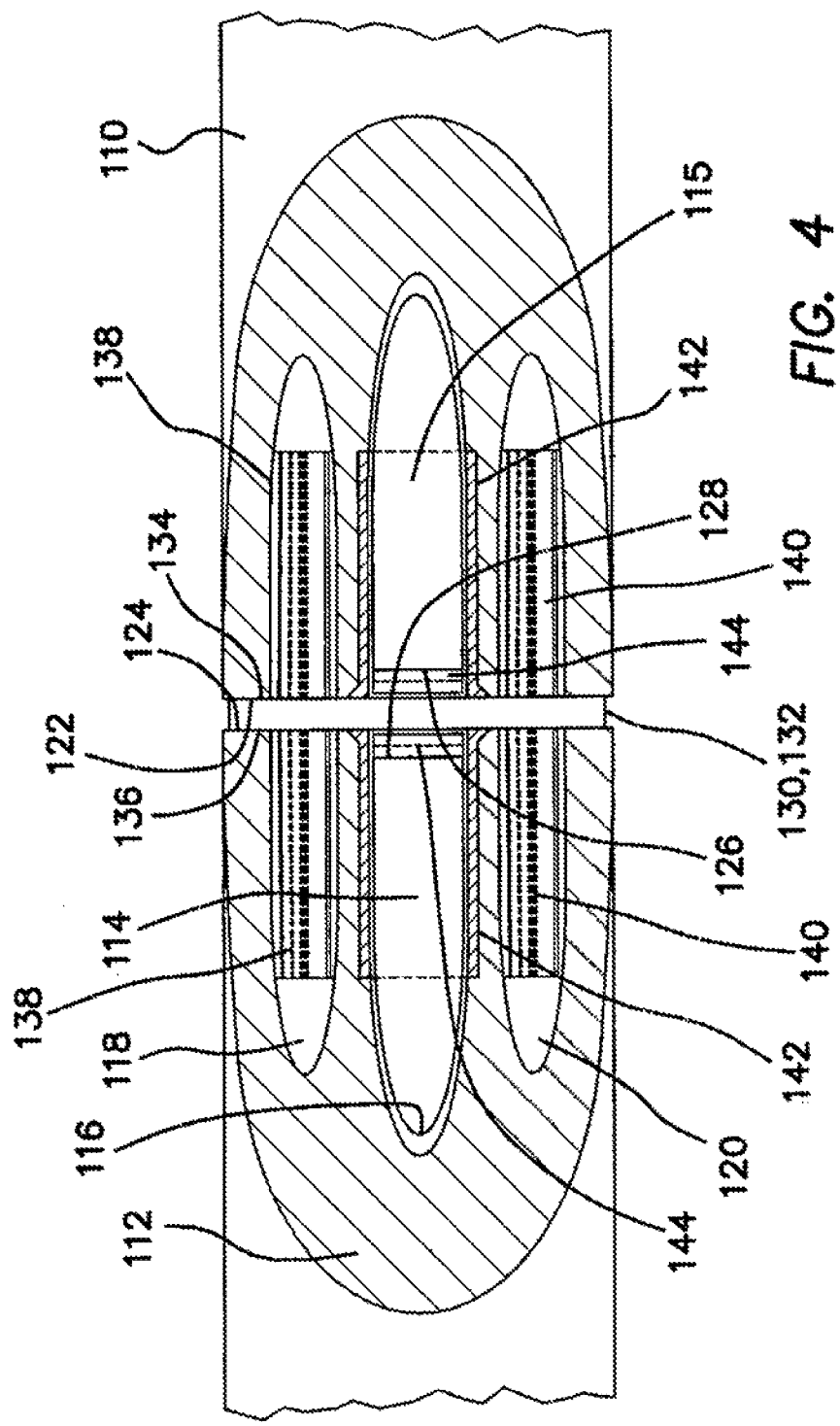
FIG. 4 is a side view of an outer ring of a surgical retractor, partially in cross section, in accordance with various aspects of the present invention.

Referring to FIGS. 3 and 4, in one aspect the second outer ring 110 includes a single monolithic coupler 130 for coupling the first 122 and second 124 ends of the first, outer component 112 of the outer ring together and to couple the first 126 and second 128 ends of the second, inner component 114 of the outer ring together. The single monolithic coupler 130 may be made of plastic or other suitable material. In one aspect, the monolithic coupler may be made of Acrylonitrile Butadiene Styrene (ABS), high density polyethylene (HDPE) or HYTREL.

The monolithic coupler includes a base portion 132 having a first face 134, a second face 136 opposing the first face, and a periphery that substantially matches the periphery of the cross-section of the first, outer component 112 of the second, outer ring 110. Each of the first 134 and second 136 faces of the base portion 132 of the monolithic coupler 130 has a first pin 138, a second pin 140 and a tube portion 142 protruding therefrom with the pins and tube portion on each face being substantially symmetrical to the pins and tube portion on the opposing face. The first 138 and second 140 pins on the first face 134 of the monolithic coupler base 132 are positioned, aligned and adapted to mate with the second 118 and third 120 lumens, respectively, at the first end 122 of the first, outer component 112 of the second, outer ring 110. Similarly, the first 138 and second 140 pins on the second face 136 of the monolithic coupler base 132 are positioned, aligned and adapted to mate with the second 118 and third lumens 120, respectively, at the second end 124 of the first, outer component 112 of the second, outer ring 110. The tube portion 142 on the first face 134 of the monolithic coupler base 132 is aligned and adapted to mate with the first lumen 116 at the first end 122 of the first, outer component 112 of the second, outer ring 110 and the tube portion 142 on the second face 136 of the monolithic coupler base 132 is aligned and adapted to mate with the first lumen 116 at the second end 124 of the first, outer component 112 of the second, outer ring 110. Each of the tube portions 142 of the monolithic coupler 130 includes an aperture 144 that is open at the end of the tube portion away from the base 132 of the monolithic coupler. Alternatively, the monolithic coupler 130 may include an aperture 144 that extends completely through the tube portion 142 on the first face 134, the base portion 132, and the tube portion 142 on the second face 136. The aperture 144 of each of the tube portions 142 of the monolithic coupler 130 is adapted to receive one of the first 126 and second 128 ends of the rigid ring 115 of the second, inner component 114 of the second, outer ring 110 of the surgical retractor 100.

The first 138 and second 140 pins on each of the first 134 and second 136 faces of the monolithic coupler base 132 tapers away from the base. The taper on the pins facilitates insertion of the pins into the respective lumens 118, 120 of the first, outer component 112 of the second, outer ring 110. The outer surface of the tube portions 142 on each of the first 134 and second 136 faces of the monolithic coupler base 132 also tapers away from the base with the taper facilitating insertion of the tube portions into the first lumen 116 of the first, outer component 112 of the second, outer ring 110. The aperture 144 of each of the tube portions 142 is tapered toward the monolithic coupler base 132 to facilitate the insertion of one of the first 126 and second 128 ends of the second, inner component 114 of the second, outer ring 110 therein.

The length of each of the tube portions 142 of the monolithic coupler 130 is sufficient to maintain the first 126 and second 128 ends of the second, inner component 114 of the second, outer ring 110 therein and to maintain the tube portions within the first, middle lumen 116 of the first, outer component 112 of the second, outer ring. Similarly, the first 138 and second 140 pins protruding from the first 134 and second 136 faces of the monolithic coupler base 132 are of sufficient length to maintain the pins in the second 118 and third 120 lumens, respectively, of the first, outer component 112 of the second, outer ring 110. Being made of Acrylonitrile Butadiene Styrene (ABS), the monolithic coupler 130 is flexible and the pins 138, 140 and tube portions 142 thereof may assume a curved shape as influenced upon by the rigid wire 115 of the second, inner component 114 of the second, outer ring 110 and by the first, outer component 112 of the second, outer ring. Alternatively, the monolithic coupler 130 may be substantially rigid and may be made by methods including die casting, metal injection molding, and/or powdered metallurgy.

The first, inner ring 102 may include a single component having an overall substantially circular shape and a substantially circular cross-section. The first, inner ring 102 may be made of a material that is softer than the material of which the first, outer component 112 of the second, outer ring 110 is made. Alternatively, the first, inner ring 102 may be made of a material having about the same hardness as the material of which the first, outer component 112 of the second, outer ring 110 is made or may be made of a material that is harder than the material of which the first, outer component of the second, outer ring is made. The sleeve 106 may be made of a flexible, semi-transparent plastic film that is coupled to the first, inner ring 102 and the second, outer ring 110.

Referring again to the first, outer component 112 of the second, outer ring 110, the cross-sectional height and width of the first, outer component may be proportionally different or varied to create lock points as the outer component is rotated about the second, inner component 112. As the sleeve 106 is rolled around the second, outer ring 110, while the outer ring is rotated, lock points prevent the outer ring from rotating back, and thus prevent the sleeve from unraveling from the second, outer ring. Different cross-sectional shapes (not shown) of the first, outer component (e.g., triangle, cross, etc.) assist in providing differing lock points. Lock points also provide incremental rotational positions for the second, outer ring, thereby providing incremental retraction of the incision or body opening. Generally symmetrical cross-sectional shapes provide substantially uniform rotational motion and lock points, thereby providing a substantially uniform "snap" feel with each incremental rotation. The lock points also help keep the first, outer component of the second, outer ring from tilting as a result of forces encountered when retracting the surgical incision or body orifice.

Figure 5:
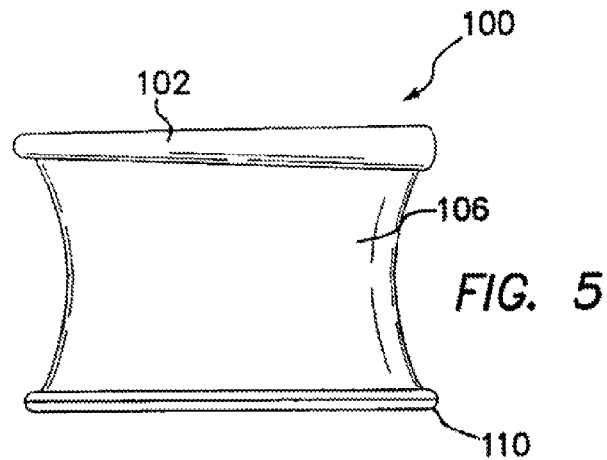
FIG. 5 is a side view of a surgical retractor in accordance with various aspects of the present invention.

The footprint of the second, outer ring 110 can be symmetrical or non-symmetrical and can vary in size and shape, such as a circle, ellipse or other suitable shape, to conform to a body type, position or size and thereby increase the working space or reduce potential interference with other instruments or ports during the laparoscopic procedure. In one aspect, the first, outer component 112 can be formed in a Mobius shape (FIG. 5) by rotating one of the first 122 and second 124 ends of the first, outer component of the second, outer ring 110 180° about the second inner component 114 of the second, outer ring and joining the first and second ends together. In this manner, the second lumen 118 at the first end 122 of the first, outer component 112 of the second, outer ring 110 couples to the third lumen 120 at the second end 124 of the outer component of the outer ring, and the third lumen 120 at the first end 122 of the outer component 112 of the outer ring couples to the second lumen 118 at the second end 124 of the outer component of the outer ring. A Mobius shape is substantially neutral relative to rotational movement of the second, outer ring 110 and thereby locking points may be reduced or removed. Similarly, the cross-sectional shape of the first, outer component 112 of the second, outer ring may be neutral or symmetrical with equal height and width dimensions.

As stated above, the first, outer component 112 may be made of a thermoplastic elastomeric material, such as HYTREL or PELLETHANE. Increasing the hardness of the material used for the first, outer component increases resistance to lock the second, outer ring 110 in position with each rotation of the outer ring. The type of material used for the first, outer component can affect the height and width of the first, outer component to provide sufficient lock points for the second, outer ring. For example, the material hardness can be reduced while the height/width cross-section ratio of the first, outer component is increased. Conversely, the material hardness can be increased while the height/width cross-section ratio of the first, outer component is reduced. The first, outer component can be extruded, injection molded, compression molded, or over-molded. Those with ordinary skill in the art will recognize that other means for creating the first, outer component may be utilized. An over-molded first, outer component is substantially neutral, in relation to stress loads, and therefore experiences a difference in forces required to produce successive snaps. The difference in forces produced by an over-molded first, outer component may facilitate the outer component in maintaining a neutral position and in snapping or rotating into the neutral position. However, an over-molded first, outer component may also resist rotation of the outer component away from the neutral position. An extruded first, outer component may have the ends produced thereby heat sealed together.

The cross-sectional profile of the second, outer ring 110 of the surgical retractor 100 may be reduced to increase the insertion angle for instruments being inserted therethrough. More particularly, the cross-sectional height and/or width of the second, outer ring may be reduced. This is particularly useful for body orifice retraction, such as rectal or vaginal retraction. The more the profile of the second, outer ring is reduced, the more difficult it becomes to roll the first, outer component of the outer ring about the second, inner component of the outer ring and a tool may be required to facilitate rolling the outer component about the inner component.

Referring again to the lumens 116, 118, 120 of the first, outer component 112 of the second, outer ring 110, the lumens may include other shapes, such as circular, polygonal, or other suitable shapes (not shown). Additionally, the first, middle lumen 116 may have detents, protuberances or other forms to interact with the second, inner component 114 of the second, outer ring 110. The second, inner component of the second, outer ring, such as the rigid wire 115, may also have detents, protrusions or other forms to interact with the first, middle lumen of the first, outer component. Both the middle lumen and rigid wire may have interacting detents, protrusions, notches or other forms. This interaction provides lock points that provide incremental rotation of the second, outer ring and retraction of the incision or body opening.

As indicated above, the first 112 and second 114 components of the second, outer ring 110 of the surgical retractor 100 may be coupled together with a monolithic coupler 130. Alternatively, the first 122 and second 124 ends of the first, outer component 112 of the second, outer ring 110 may be coupled together with at least one coupler (not shown). The at least one coupler may include a substantially longitudinal rod having a barb on each end (not shown). The at least one coupler for coupling the first and second ends of the first, outer component may include a first coupler and a second coupler. The first coupler couples the first and second ends of the second, top lumen 118 together in a snap-fit relationship while the second coupler couples the first and second ends of the third, bottom lumen 120 together in a snap-fit relationship. The couplers may be made of plastic or other suitable material. Similarly, the first and second pins on the first and second sides of the monolithic coupler base 132 may include barbs (not shown) to facilitate retention of the pins 138, 140 in the second and third lumens 118, 120 of the first, outer component 112 of the second, outer ring 110.

Figure 6:
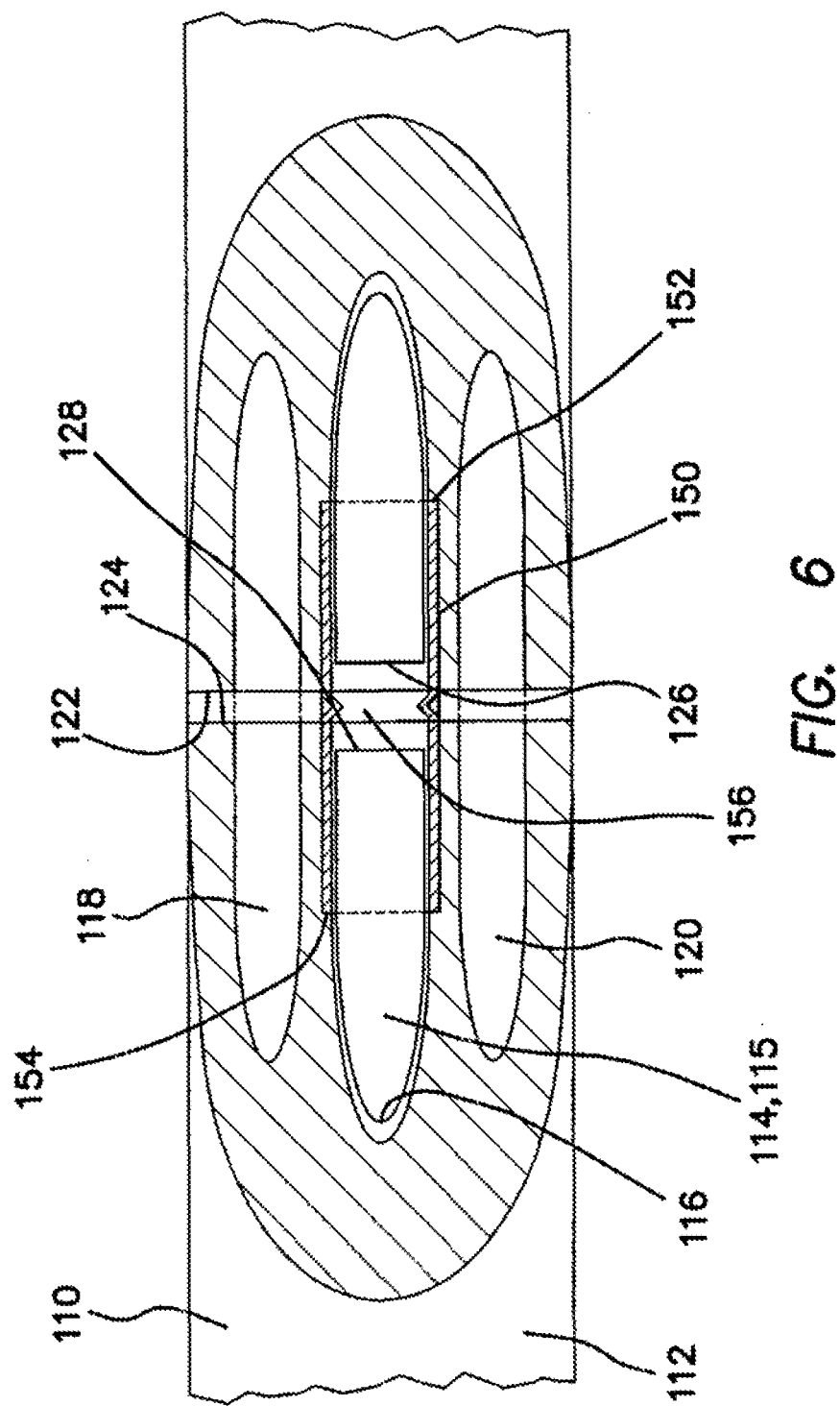
FIG. 6 is a side view of an outer ring of a surgical retractor, partially in cross section, in accordance with various aspects of the present invention.

Referring to FIG. 6, the first 126 and second 128 ends of the second, inner component 114 of the second, outer ring may be coupled together with a ferrule 150 when using means other than the monolithic coupler 130 to couple together the first 122 and second 124 ends of the first, outer component 112 of the outer ring 110. The ferrule 150 is a metal tube that the first 126 and second 128 ends of the second, inner component 114, such as the rigid wire 115, may be inserted into. More particularly, the first end 126 of the wire 115 may be inserted into a first end 152 of the ferrule 150 and the second end 128 of the wire may be inserted into a second end 154 of the ferrule. Each of the first 152 and second 154 ends of the ferrule 150 may be crimped onto the rigid wire 114, 115 therein. The ferrule is not compliant or resilient. The ferrule does not flex, yield or deform. The ferrule has an inner diameter that is larger than the diameter of the rigid wire. The ferrule is of sufficient length to retain the first and second ends of the second component of the second, outer ring of the surgical retractor.

As indicated above, the second, inner component 114 of the second, outer ring 110 may be made of a rigid wire 115 that is bent into a generally circular shape. The wire thickness for the rigid wire may be between about 0.25-12.70 mm (0.010-0.500 inches) in diameter. The wire thickness may vary in correlation to the wound or body opening size and the device size. For example, the larger the wound or body opening size is, the larger the wire size is. The wire diameter can also correlate to the wire material. For example, as the hardness of the material of the wire is increased, the wire diameter may be reduced. One or more wires having differing lengths may be used and form a ring when bundled together. One or more wire segments, such as barrels, can be aligned from end to end within the lumen 116 of the first, outer component 112 to form a ring. The rigid wire may include one wire or more wires that may be bundled or bonded together. The wires may be braided or overlapped together. One or more wires may also be wound one or more times through the first, middle lumen 116 of the first, outer component 112 of the second, outer ring 110.

Figure 7:
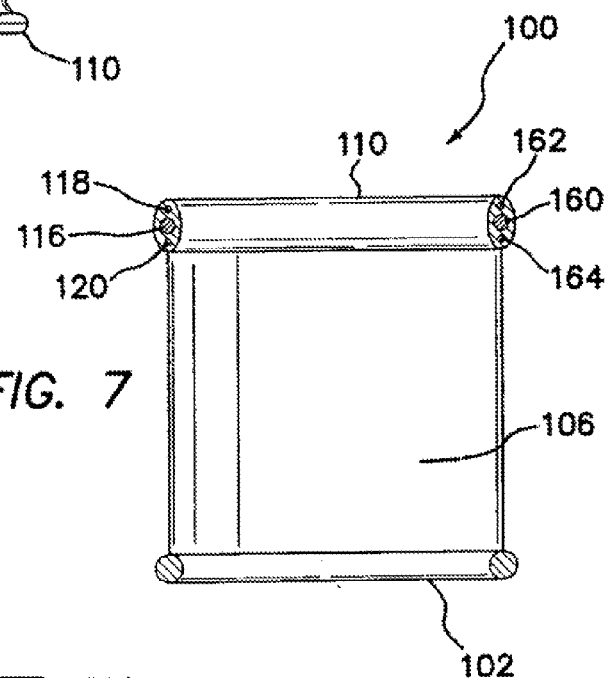
FIG. 7 is a side view of a surgical retractor, in cross section, in accordance with various aspects of the present invention.

Referring to FIG. 7, in one aspect, the wire positioned in the first, middle lumen 116 of the first, outer component of the second, outer ring is a first wire 160 of the second, inner component 114 of the outer ring. In this aspect, the second, inner component of the second, outer ring includes a second, split wire 162 positioned in one of the second, top lumen 118 and the third, bottom lumen 120 of the outer component 112 of the outer ring 110. Alternatively, the second, outer ring 110 may include the first wire 160 in the first, middle lumen 116 of the first, outer component 112 of the outer ring, a second, split wire 162 in the second lumen 118 of the outer component and a third, split wire 164 in the third lumen 120 of the outer component. The split in the second and/or third wire creates a first end and a second end of the second and/or third wire. With the first, middle lumen 116 including the first wire 160, rolling the sleeve 106 around the second, outer ring 110 includes turning the first, outer component 112 of the outer ring around the first wire. The first wire 160 functions as an axle about which the first, outer component 112 of the second, outer ring 110 is turned. The periphery of the second 162 and/or third 164 wire expands when it is turned outside of the first wire 160 and contracts when it is turned inside of the first wire.

In one aspect, the second 162 and/or third 164 wire includes a space between the first and second ends of the respective wire. When positioned within the second lumen 118 of the first, outer component 112 of the second, outer ring 110, the first end of the second wire is positioned proximate the first pin 138 protruding from the first face 134 of the monolithic coupler 130 and the second end of the second wire is positioned proximate the first pin 134 protruding from the second face 136 of the monolithic coupler. Likewise, when the third wire 164 is present in the third lumen 120, the first end of the third wire is positioned proximate the second pin 140 protruding from the first face 134 of the monolithic coupler 130 and the second end of the third wire is positioned proximate the second pin 140 protruding from the second face 136 of the monolithic coupler. In one aspect, the space between the first and second ends of the second 162 and/or third 164 wire is sufficient to permit the periphery of the second and/or third wire to contract to a smaller size when the respective wire is rolled inside the first wire 160 during rolling of the second, outer ring 110 without at least one of the first and second ends of the respective wire contacting the first 138 and/or second 140 pins of the monolithic coupler 130.

The second 162 and third 164 wires may be substantially identical to each other and have a wire thickness smaller than the wire thickness of the first wire 160 positioned in the first lumen 116 of the first, outer component 112 of the second, outer ring 110. More particularly, each of the second 162 and third 164 wires may have a wire thickness of about 0.25-6.35 mm (0.010-0.250 inches) in diameter. Having a wire positioned in at least one of the second 118 and third 120 lumens of the first, outer component 112 of the second, outer ring 110 facilitates "snapping" of the outer ring when turning the outer ring and holds the outer ring substantially in the neutral position against high retraction forces.

The rigid wire 115 for the second, inner component 114 of the second, outer ring 110 may include a straight rigid wire. The straight rigid wire may be inserted into the first, middle lumen 116 of the first, outer component 112. When the ends 122, 124 of the first, outer component 112 of the second, outer ring 110 are joined, the wire 115 is forced to assume a substantially circular shape, placing the wire in a preloaded condition. The preloaded condition of the wire causes the wire to maintain a tendency to straighten out. The tendency of the wire to straighten out helps the second, outer ring 110 maintain a circular shape when the ends 122, 124 of the first, outer component 112 of the outer ring are joined.

The rigid wire 115 of the second, inner component of the second, outer ring may be bent and inserted into the first, middle lumen 116 of the first, outer component 112. As indicated above, the first 126 and second 128 ends of the rigid wire 115 may be coupled together by the monolithic coupler 130 or the ferrule 150. Alternatively, the first 126 and second 128 ends of the rigid wire 115 may be coupled together by other means, such as being welded, soldered, adhered or otherwise bonded together. Windows or cutouts may be provided in the first, outer component of the second, outer ring to facilitate the coupling of the first and second ends of the rigid wire together. Other means for coupling the first and second ends of the rigid wire of the second, inner component 114 of the second, outer ring 110 together include providing interlocks on the ends of the rigid wire. The interlocks may include notches, detents or other similar defects on the wire ends to create or increase the mechanical interlock of the wire ends. Ball and socket, opposing hooks, spring pins, or other interlock configurations may also be provided to lock the first and second ends of the wire together. Alternatively, in one aspect the first and second ends of the rigid wire may be left uncoupled.

The rigid wire 115 of the second, inner component 114 of the second, outer ring 110 may include straight end sections to prevent or reduce movement of the ferrule 150 relative to the ring. Notches, detents or other similar defects may be introduced on the wire ends to create or increase the mechanical interlock between the wire and the monolithic coupler 130 or the ferrule 150.

The second, inner component 114 of the second, outer ring 110 may include a pre-bent, continuous rigid ring 115. The first, outer component 112 of the second, outer ring 110 may include one or more slits extending from an external surface of the outer component to the first, middle lumen 116 of the outer component to facilitate insertion of the continuous rigid ring into the middle lumen. The slit may extend the entire length or periphery of the first, outer component, thereby permitting the continuous rigid ring to be inserted into the first, middle lumen of the outer component. With the second, inner component of the second, outer ring positioned in the first, middle lumen of the first, outer component of the outer ring, the slit may be closed through heat-sealing, adhesive, or by other bonding techniques that are well known in the art.

The rigid wire 115 of the second component 114 of the second, outer ring 110 may be positioned external and substantially adjacent the first component 112 of the outer ring and the first and second components may be stitched together (not shown). In this manner, the rigid wire is positioned off-center of the first component. With the rigid wire positioned off-center of the first, inner component of the second, outer ring, the diameter of the first, outer component of the outer ring may be expandable and/or contractible. The first component may be made of a soft material that allows the first component to stretch in tension and/or reduce in compression while being rotated about the rigid wire of the second component.

As stated above, the second, inner component 114 of the second, outer ring 110 may include a rigid wire 115 having its ends 126, 128 joined together with a ferrule 150. For example, each end of the wire may be inserted into the ferrule and the ferrule may be crimped in the center or on one or both ends of the ferrule. A center crimp, like an end crimp, prevents the ferrule from sliding around the wire and bonds the wire to the ferrule. The ends of the ring may be force fitted into the ferrule. The ferrule diameter corresponds to the diameter of the rigid wire. The ferrule diameter can vary. The generally curved rigid wire being forced into the generally straight ferrule causes the ferrule and wire to resist separation from each other.

The ferrule 150 may be made of 304 CRES and be TIG welded to the ring, however, those with ordinary skill in the art will recognize that other suitable materials and coupling means may be utilized. More particularly, the ferrule may be made of steel or other material that corresponds to the wire material. Welding the ferrule to the wire 115 may produce tighter tolerances for the diameter or perimeter of the wire relative to welding the ends 126, 128 of the wire together. Corresponding notches, detents or other similar defects may be introduced on the wire ends to create or increase the crimping or welding connection between the wire and the ferrule.

The length of the ferrules 150 may vary. For example, the ferrule may be similar in length and shape to the wire 115 with the wire extending through the lumen 156 of the ferrule. Those with ordinary skill in the art will recognize that other lengths and shapes may be used. A split (not shown) may be provided in the ferrule and positioned offset from the split in the wire. For example, the splits in the ferrule and wire can be positioned about 180° apart from each other. Again, those with ordinary skill in the art will recognize that the splits in the ferrule and wire may be offset at other positions.

Figure 8:
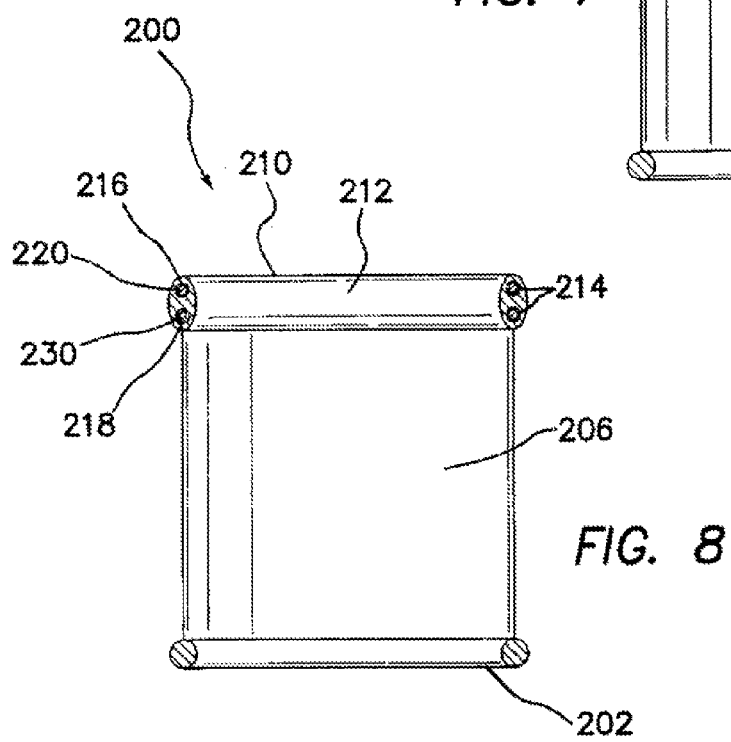
FIG. 8 is a side view of a surgical retractor, in cross section, in accordance with various aspects of the present invention.

Referring to FIG. 8, in one aspect, the second, outer ring 210 of the surgical retractor 200 includes a first, outer component 212 having a substantially oval cross-section including a first lumen 216 and a second lumen 218. Each of the first 216 and second 218 lumens is positioned substantially along the major axis of the oval with the first lumen positioned on a first side of the minor axis of the oval and the second lumen positioned on a second, opposite side of the minor axis of the oval. The second, inner component 214 of the second, outer ring 210 of the surgical retractor 200 includes a first substantially noncompliant, split hoop 220 positioned in the first lumen 216 of the first, outer component 212 of the outer ring and a second substantially noncompliant, split hoop 230 positioned in the second lumen of the outer component. Each of the first 220 and second 230 split hoops may include a hoop having a single split about its periphery with the split creating a first end of the split hoop and a second end of the split hoop. In its neutral position, the first and second ends of the respective split hoops substantially abut each other.

The first 220 and second 230 split hoops may be made of metals, such as stainless steel, piano wire heat treated to a spring temper, or other metals that produce a substantially noncompliant hoop. The first and second split hoops may also be formed of rigid polymeric materials through molding, machining, and other processes that are well known in the art. The substantially noncompliant split hoops may also be formed of other suitable rigid materials that are well known in the art.

The spacing between the first 216 and second 218 lumens of the first, outer component 212 of the second, outer ring 210 and the cross-sectional size of the first 220 and second 230 split hoops of the second, inner component 214 of the outer ring positioned within the first and second lumens dictates the effectiveness of the surgical retractor. During use, the second, outer ring of the surgical retractor 200 is rolled down by forcing one of the split hoops open, thereby causing a space between the first and second ends of the hoop, and around the other split hoop. In this manner, one of the rigid split hoops works as an axle or center of rotation for the other split hoop. By placing the two split hoops further apart or by increasing the strength of the split hoops, greater force is required to rotate the second, outer ring of the surgical retractor. The spacing between the first and second lumens and the cross-sectional size of the first and second split hoops may, therefore, be selected for a desired balance between the force required to rotate the second, outer ring against the tendency of the outer ring to unroll because of the force imparted on the outer ring by a retracted incision or body opening.

The cross-sectional diameter of the first 220 and second 230 split hoops may vary depending on the cross-section of the first outer component 212 of the second, outer ring 210 and on the size of the incision or body opening to be retracted. In one aspect, for incisions 5-9 cm in length, 3.0 mm diameter wire may be utilized. Each of the first and second hoops may be made of a wire having a thickness of about 0.25-6.35 mm (0.010-0.250 inches) in diameter.

Figure 13:
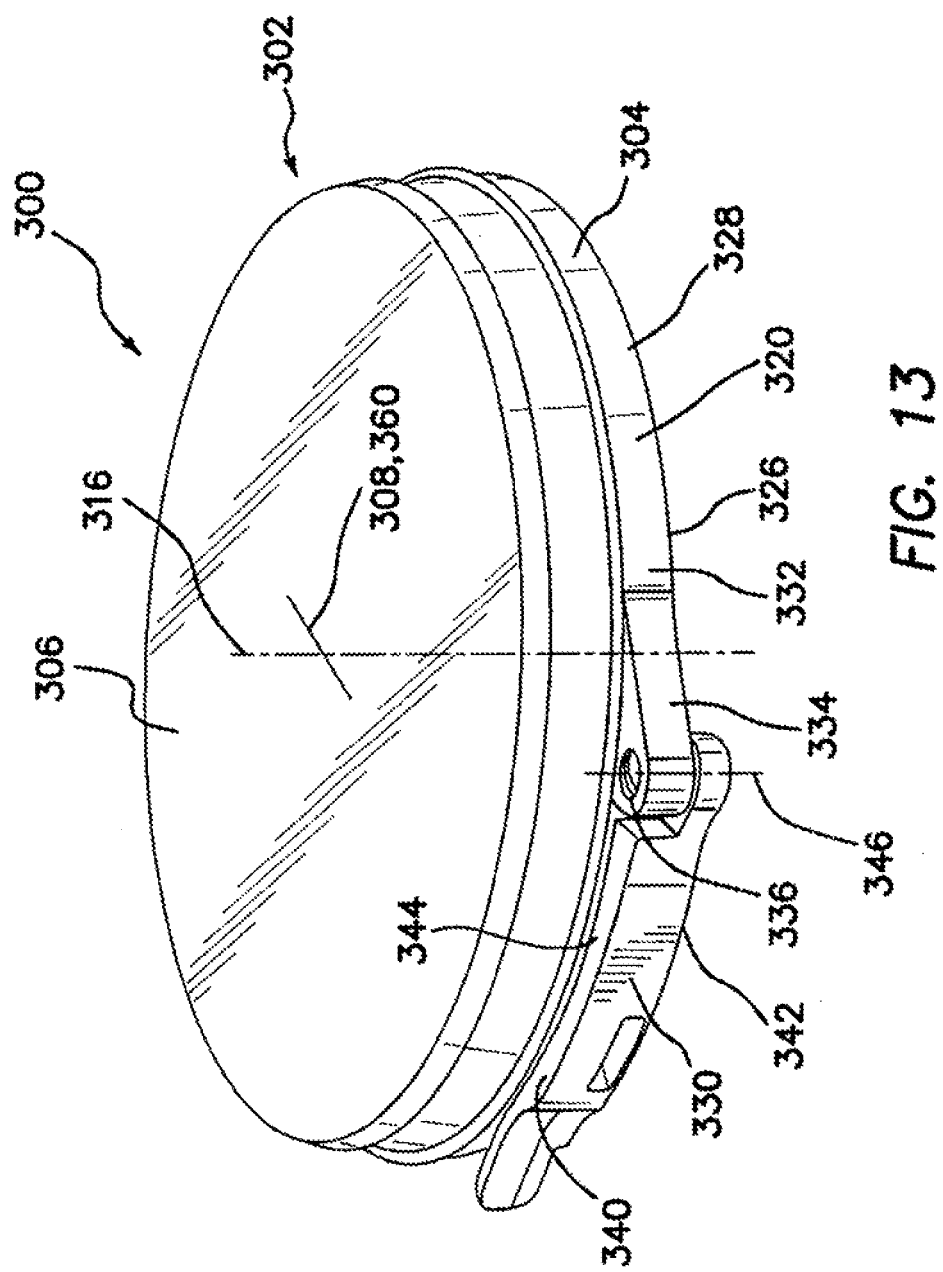
FIG. 13 is a perspective view of a gel cap for use with a surgical retractor in accordance with various aspects of the present invention.

The first 220 and second 230 split hoops of the second, inner component 214 of the second, outer ring 210 of the surgical retractor 200 may be formed of, for example, full-hard temper wire and to a peripheral size that is smaller than that which the first, outer component 212 of the outer ring would force the first and second split hoops into. In this manner, the first, outer component 212 of the second, outer ring 210 is held closed and the first 220 and second 230 split hoops control the orientation of the outer component during use. To attain a peripheral size of the first 220 and second 230 split hoops that is smaller than that which the first, outer component 212 of the second, outer ring 210 would force upon the first and second split hoops, the split hoops may be formed with first and second end portions of each of the split hoops overlapping each other. In one aspect, the materials of which the first, outer component 212 of the second, outer ring 210 is made, combined with the size of the first 216 and second 218 lumens of the outer component, do not permit the first and second end portions of the split hoops to overlap each other within the lumens. When the first 220 and second 230 split hoops are assembled with the first, outer component 212 of the second, outer ring 210, the overlap between the end portions of the first and second split hoops is removed and the first and second ends of each of the split hoops substantially abut each other with a spring force that causes the second, outer ring to remain closed. In this manner, the first 220 and second 230 split hoops facilitate stability of the second, outer ring 210 so that the cross-section of the first, outer component 212 remains vertical at 0° and 180° orientations, thereby facilitating the attachment of a cap 302 (FIG. 13) to the second, outer ring 210 of the surgical retractor 200. In one aspect, split hoops of varying cross-sectional size may be positioned within the first 216 and second 218 lumens of the first, outer component 212 of the second, outer ring 210 to create retractors that have a bias to determinable orientations.

Since each of the first 220 and second 230 split hoops has substantially abutting first and second ends, each of the split hoops functions as an axle about which the first, outer component 212 may turn for half a rotation, or 180°. More particularly, the second, outer ring 210 may be rolled such that the first split hoop 220 is rolled outside the second split hoop 230 with the periphery of the first split hoop expanding to clear the second split hoop. With continued rolling of the second, outer ring 210, the second split hoop 230 may be rolled outside the first split hoop 220 with the periphery of the second split hoop expanding to clear the first split hoop. These steps may be repeated until the incision or body opening is retracted to the desired degree.

In one aspect, the first split hoop 220 of the second, inner component 214 of the second, outer ring 210 may include a space (not shown) positioned between the first and second ends of the first split hoop, while the first and second ends of the second split hoop 230 may substantially abut each other. When the first split hoop 220 is rolled inside the second split hoop 230 during rolling of the second, outer ring 210, the first split hoop contracts, thereby reducing the space between the first and second ends of the first split hoop and reducing the perimeter of the first split hoop to a size smaller than the second split hoop. With the perimeter of the first split hoop 220 reduced, the first split hoop may roll through the second split hoop 230. In one aspect, each of the first 220 and second 230 split hoops may include a space positioned between the first and second ends of the respective split hoop. The first 220 and second 230 split hoops are positioned within the first 216 and second 218 lumens, respectively, of the first, outer component 212 of the second, outer ring 210 with the space in the first split hoop circumferentially offset from the space in the second split hoop to substantially prevent having a weak or collapsing section of the second, outer ring of the surgical retractor 200. When the first split hoop 220 is rolled inside the second split hoop 230 during rolling of the second, outer ring 210, the first split hoop contracts and the second split hoop expands. Likewise, when the second split hoop 230 is rolled inside the first split hoop 220, the second split hoop contracts and the first split hoop expands. With each of the first 220 and second 230 split hoops having a space between respective first and second ends, during rolling of the second, outer ring 210 the axis of rotation is between the first and second split hoops, or between the first 216 and second 218 lumens.

The second, outer ring 210 of the surgical retractor 200 may be formed by transforming an extruded elastomeric tube into a circular ring by placing the first 220 and second 230 split hoops into the first 216 and second 218 lumens of the first, outer component 212 of the outer ring. This is accomplished by inserting one of the first and second ends of the first split hoop 220 into the first lumen 216 of the first, outer component 212 and inserting one of the first and second ends of the second split hoop 230 into the second lumen 218 of the first, outer component. Each of the first 220 and second 230 split hoops is continually fed into the respective lumen 216, 218 until each of the split hoops is substantially entirely within the respective lumen. The first, outer component 212 takes on the shape of the split hoops 220, 230 positioned in the first 216 and second 218 lumens thereof.

It is appreciated that the first, outer component 212 of the surgical retractor 200 can be designed in various configurations and sizes to achieve various retraction rates and/or to conform to different body surfaces. The first 216 and second 218 lumens may have cross-sections of different geometries, such as circular, oval, triangular, rectangular, any geometric shape with multiple sides, etc. The first 220 and second 230 split hoops may also have cross-sections of different geometries, such as circular, rectangular, oval, triangular, any geometric shape with multiple sides, etc. Advantages of the above embodiments of the invention include improved retraction adjustability and stability.

The footprint of the second, outer ring 210 can be symmetrical or non-symmetrical and can vary in size and shape, such as a circle, ellipse or other suitable shape, to conform to a body type, position or size and thereby increase the working space or reduce potential interference with other instruments or ports during the laparoscopic procedure. In one aspect, the first, outer component 212 can be formed in a Mobius shape by twisting the first end of the first, outer component of the second, outer ring 180° relative to the second end of the first, outer component and joining the first and second ends together. In this manner, the first lumen 216 at the first end of the first, outer component 212 of the second, outer ring 210 couples to the second lumen 218 at the second end of the outer component of the outer ring, and the second lumen at the first end of the first, outer component of the second, outer ring couples to the first lumen at the second end of the outer component of the outer ring.

In one aspect, the second, outer ring 210 of the surgical retractor 200 may include an oval footprint. The first, inner ring 202 of the surgical retractor may also include an oval footprint. During use, the oval outer ring 210 can be set either perpendicular to the incision or parallel to the incision. An oval outer ring may have a substantially circular cross-section, or other substantially neutral cross-section. With the second, outer ring having an oval footprint, the sleeve 206 will not unravel from the outer ring 210 following winding of the sleeve around the outer ring. The straight portions of the oval outer ring can include handlebar-type grips for winding the sleeve.

Figure 9:
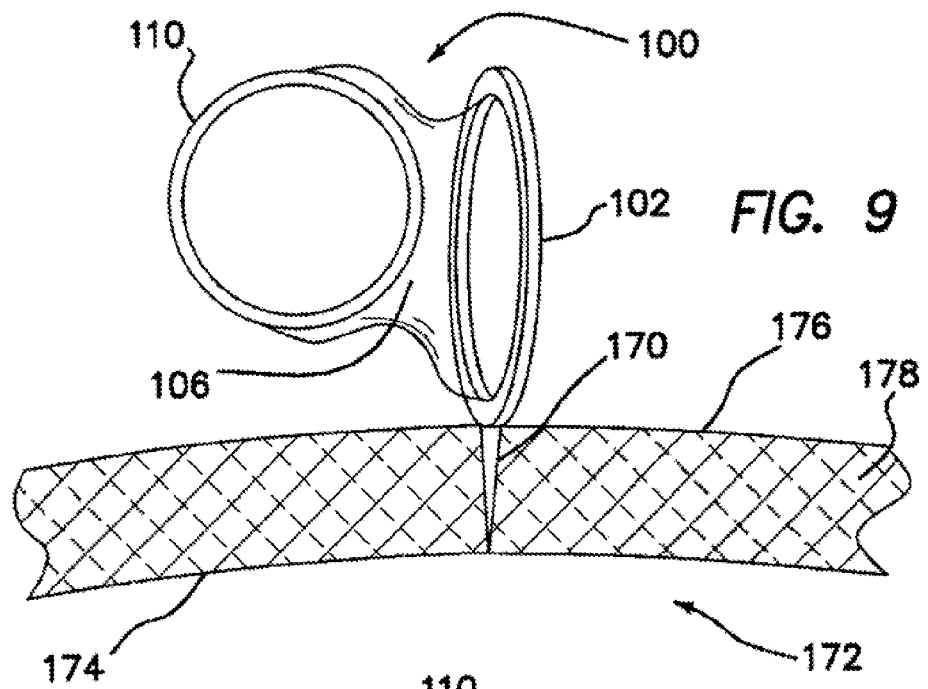
FIG. 9 is a side view of a surgical retractor in accordance with various aspects of the present invention being placed in a body wall.
Figure 10:
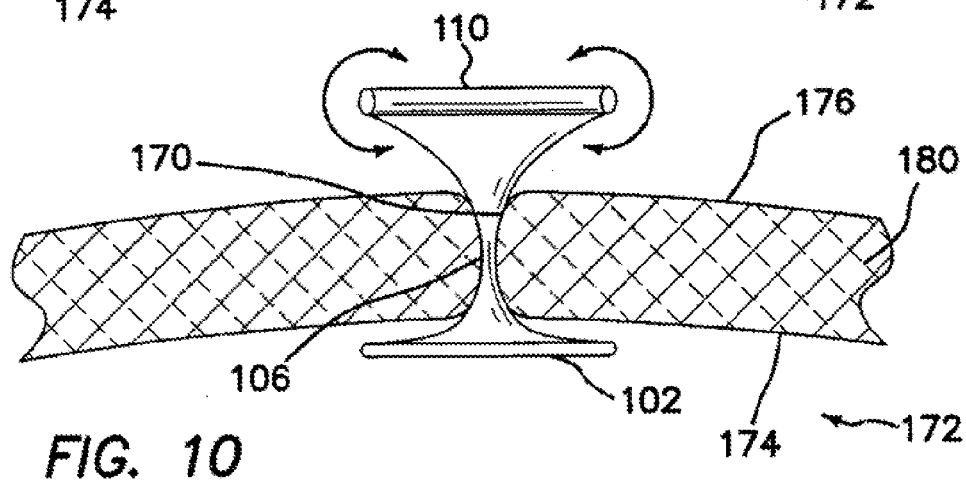
FIG. 10 is a side view of a surgical retractor in accordance with various aspects of the present invention being placed in a body wall.
Figure 11:
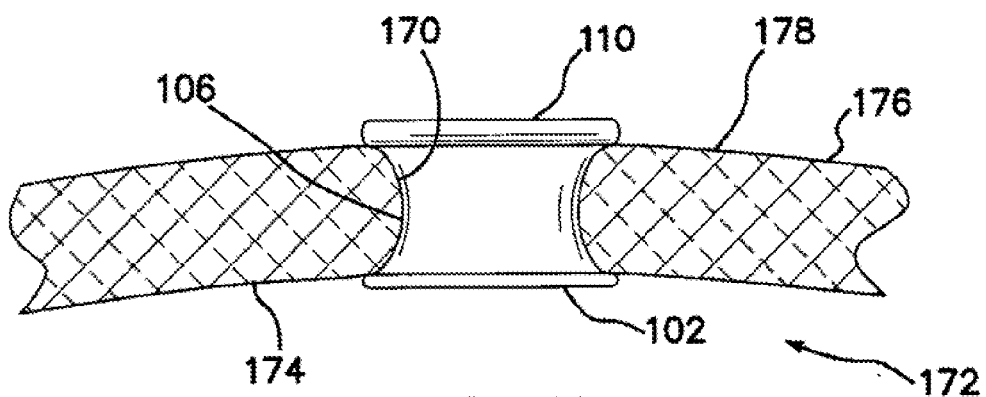
FIG. 11 is a side view of a surgical retractor in accordance with various aspects of the present invention being placed in a body wall.

Referring to FIGS. 9-11, in use a surgical retractor 100 is inserted into an incision 170 or body orifice by folding the first, inner ring 102 into an oval shape, or other shape, and urging it through the incision or body orifice. Once the first, inner ring 102 is fully within an associated body cavity 172, such as an abdominal cavity, it is allowed to resume an original, substantially circular condition, or other original shape, and pulled upward against the inner surface 174 of the body cavity. When the first, inner ring 102 is fully in place, the first, outer component 112 of the second, outer ring 110 is rolled about the second, inner component 114 of the outer ring, thereby rolling the sleeve 106 about the second, outer ring and tensioning the sleeve to retract the incision 170 or body orifice. The second, outer ring 110 is rolled until the outer ring, with the sleeve 106 wrapped around it, is substantially in contact with the exterior surface 176 of the body wall 178. When the second, outer ring 110 with the sleeve 106 wrapped around it is in contact with the exterior surface 176 of the body wall 178, the second, outer ring of the retractor is sufficiently rigid that it maintains the incision 170 or body opening substantially fully retracted. Moreover, when the second, outer ring 110 with the sleeve 106 wrapped around it is in contact with the exterior surface 176 of the body wall 178, the second, outer ring of the surgical retractor 100 is not flexible or likely to yield under the forces normally experienced during use of the surgical retractor. The rigid second, outer ring 110 facilitates the provision of 360° atraumatic retraction of the incision 170 or body opening. The surgical retractor 100 is a durable device that provides reliable protection of the incision 170 or body opening.

Figure 12:
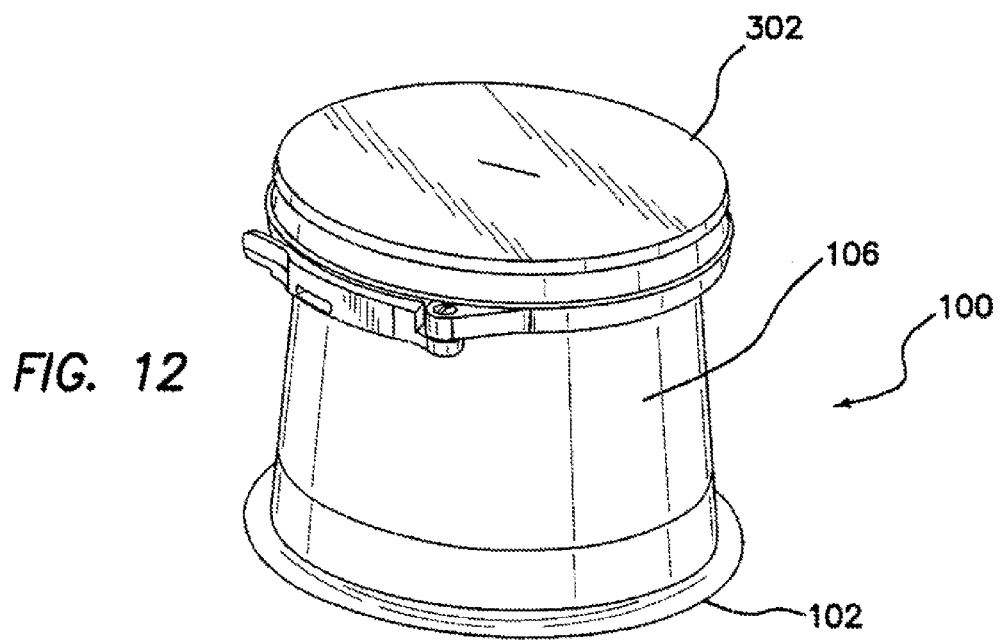
FIG. 12 is a perspective view of a surgical retractor with a gel cap in accordance with various aspects of the present invention.

Referring to FIG. 12, a lid 300 may be coupled to the second, outer ring 110 to maintain pneumoperitoneum. The lid 300 may be removed to provide access into the body cavity 172. The lid 300 may also be transparent so as to allow viewing into the body cavity 172 without removal of the lid. One such lid is a gel cap 302. The cross-sectional shape of the first, outer component 112 of the second, outer ring 110 of the surgical retractor includes a shape that substantially prohibits the gel-cap 302 from being partially or incorrectly coupled to the second, outer ring of the surgical retractor. Such cross-sectional shapes include oval and rectangular, or other of numerous cross-sectional shapes that provide the same functionality.

Referring to FIGS. 13-25, a surgical access device 300, such as a gel pad or a gel cap 302, is used to seal the opening between the body cavity and the area outside the body cavity while providing access into the body cavity from outside the body cavity. More particularly, the gel cap 302 couples to the outer ring of the surgical retractor. The gel cap 302 includes a cap ring 304 that couples to the outer ring 110 of the surgical retractor 100 and a gel pad 306 coupled to the cap ring. The gel pad 306 is made of a gel material and includes an access portion 308 or passage through the gel for providing a passage from external the body to the body cavity 404. In one aspect, the access portion 308 may include a plurality of intersecting dead-end slits 360, 362. Additionally, instruments may be inserted directly through the gel pad 306 away from the access portion 308, thereby creating additional access portions in the gel pad. In one aspect there is no access portion provided and the instruments are inserted directly through the gel pad 306, thereby creating access portions during use. The access portion 308 forms an instrument seal in the presence of an instrument, such as the arm of a surgeon, inserted therethrough and a zero seal in the absence of an instrument inserted therethrough. The gel provides a gas tight seal around a variety of shapes and sizes of hands or instruments inserted therethrough. The gel pad 306 provides trocar access, both through the access portion 308 and directly through the gel pad 306, which also enables the introduction of instruments.

The gel cap 302 maintains pneumoperitoneum during multiple hand and/or instrument exchanges and is configured to substantially prevent unintentional loss of pneumoperitoneum. The gel cap 302 also provides substantially continuous access and visibility. The gel cap 302 includes a small profile for limited body cavity space.

Figure 14:
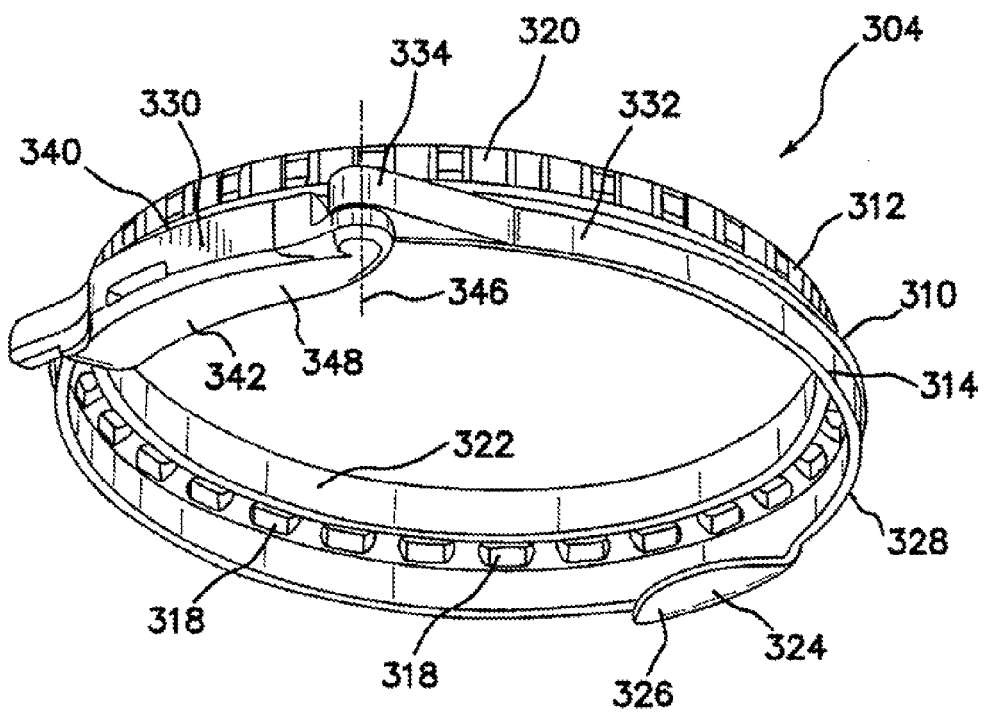
FIG. 14 is a perspective view of a gel cap for use with a surgical retractor in accordance with various aspects of the present invention.
Figure 15:
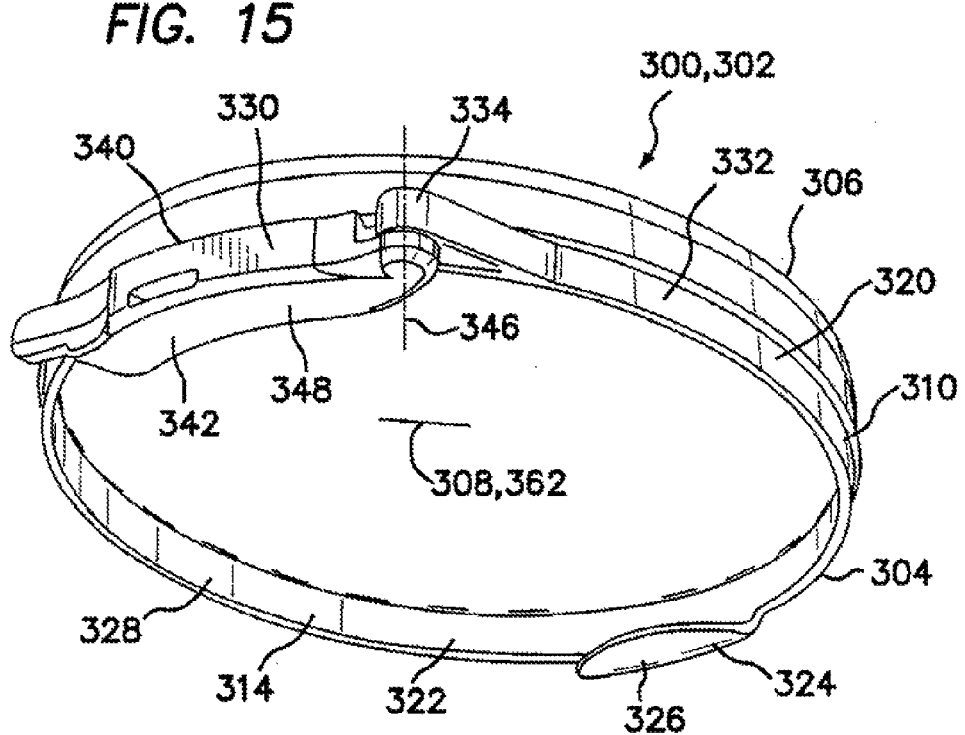
FIG. 15 is a perspective view of a gel cap for use with a surgical retractor in accordance with various aspects of the present invention.
Figure 16:
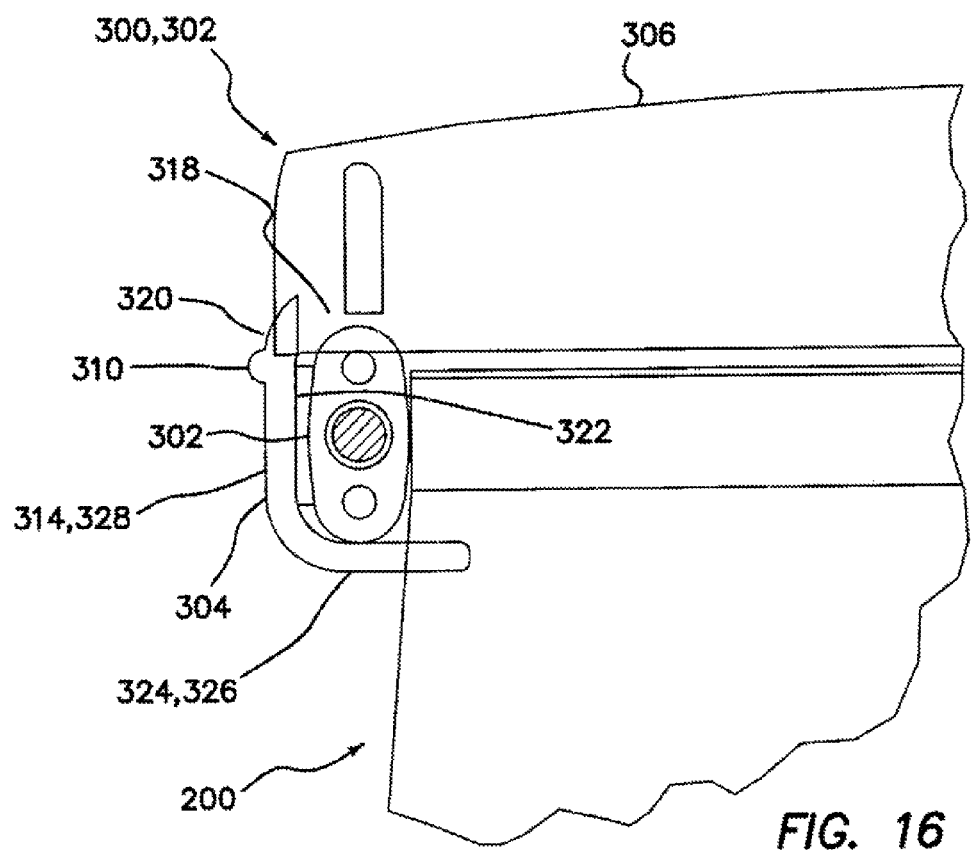
FIG. 16 is a side view, partially in cross section, of a surgical retractor and a gel cap in accordance with various aspects of the present invention.
Figure 17:
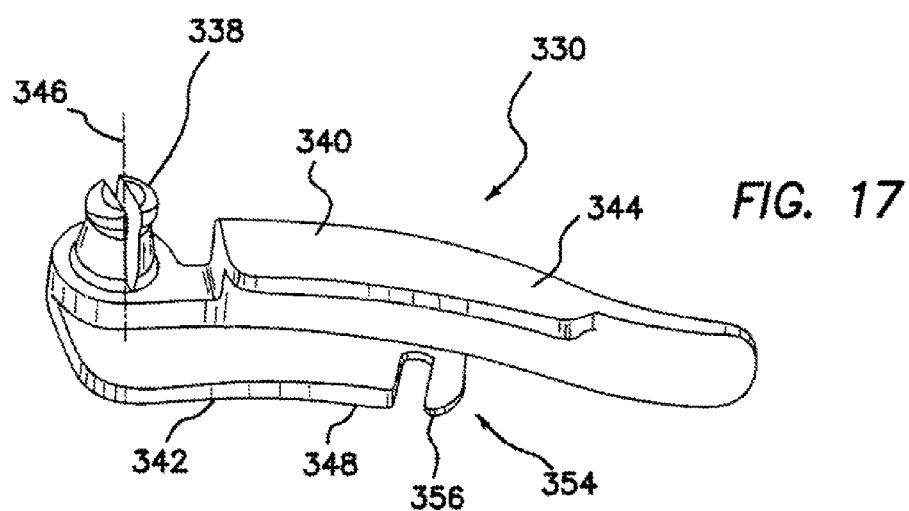
FIG. 17 is a perspective view of a latch of a gel cap for use with a surgical retractor in accordance with various aspects of the present invention.
Figure 18:
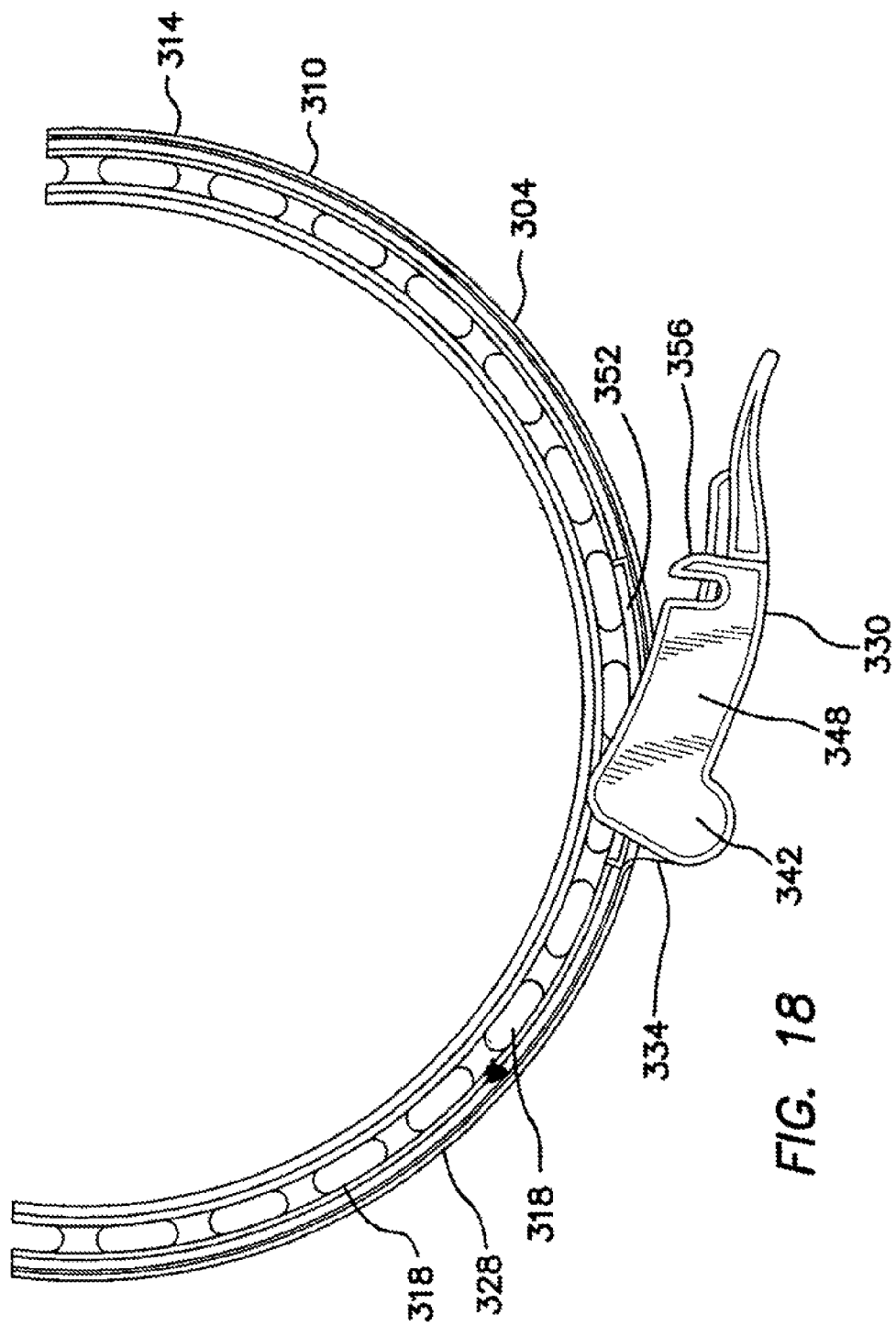
FIG. 18 is a partial bottom view of a cap ring portion of a gel cap for use with a surgical retractor in accordance with various aspects of the present invention.
Figure 19:
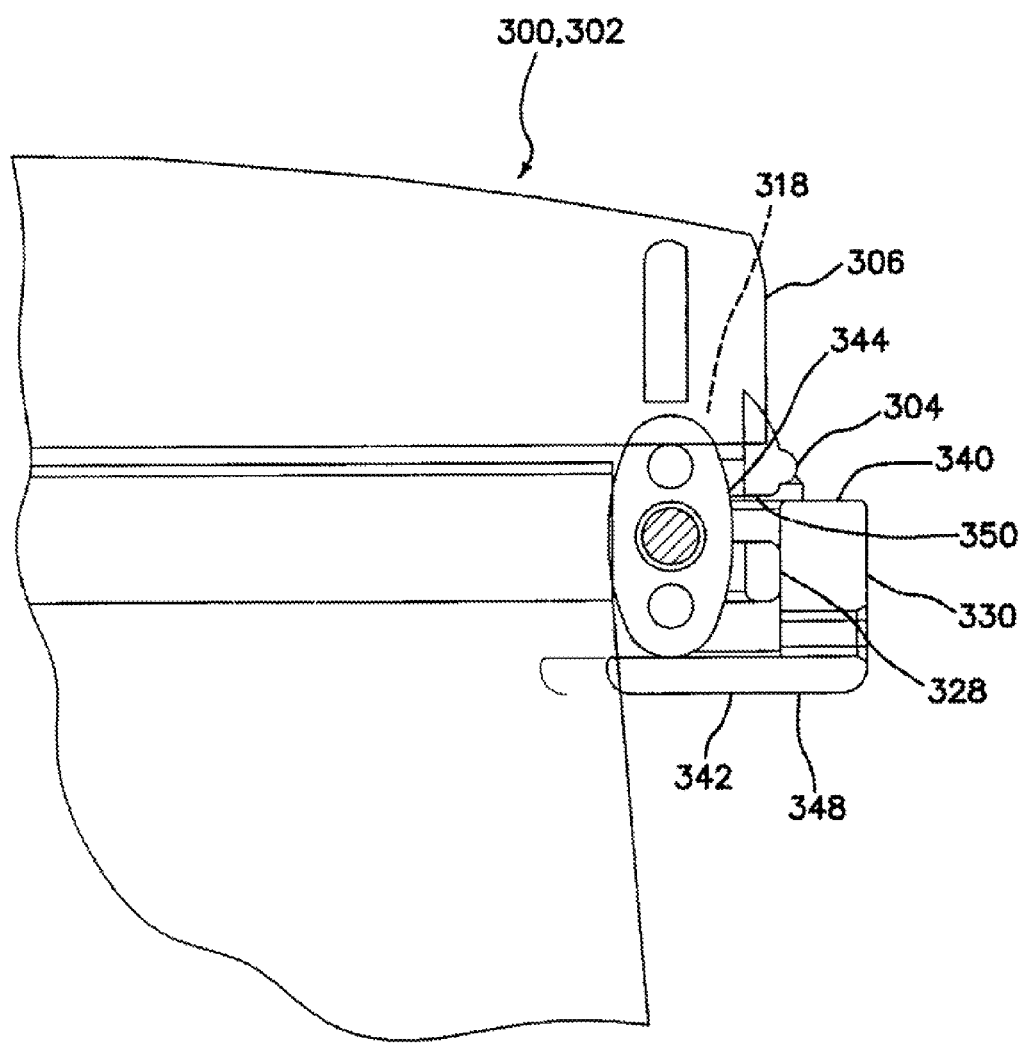
FIG. 19 is a side view, partially in cross section, of a surgical retractor and a gel cap in accordance with various aspects of the present invention.

In one aspect, to combine the gel pad 306 with the cap ring 304, the cap ring may be placed into a mold that includes the shape of the desired gel pad and uncured gel is added to the mold. Referring to FIG. 14, in one aspect, the cap ring 304 includes a substantially cylindrical ring 310 having a first, proximal portion 312, a second, distal portion 314 and a longitudinal axis 316 extending through the proximal and distal portions. The gel pad 306 is positioned at the proximal portion 312 of the cap ring 304. The proximal portion 312 of the cap ring 304 may include a plurality of apertures 318 distributed about the periphery of the cap ring. The apertures 318 may extend through the wall of the proximal portion 312 of the cap ring 304. Sufficient gel may be added to the mold to cover and fill the apertures 318 (see FIG. 15). When adding uncured gel into the mold, the gel flows through the apertures 318 and remains in the apertures. Also, for reasons that will be described below, sufficient gel may be added to the mold to extend into the distal portion 314 of the cap ring 304. When the gel pad 306 is cured, the gel in the apertures 318 connects the gel at the outer portion 320 of the cap ring 304 to the gel at the inner portion 322 of the cap ring, thus forming a mechanical lock between the gel and the cap ring. Alternatively, as will be described in more detail below, other means may be used to couple the gel pad 306 to the cap ring 304, such as separately forming a gel slug 306 and coupling the gel slug to the inner surface of the proximal portion 312 of the cap ring 304.

In one aspect, the distal portion 314 of the cap ring 304 may be substantially cylindrical and configured to receive the outer ring 110 of the surgical retractor 100. In one aspect, the distal portion 314 of the cap ring 304 includes a lip 324 at the distal end 326 thereof (see FIG. 14). The lip 324 curves radially inwardly from the wall 328 of the distal portion 314 of the cap ring 304 and extends around a portion of the periphery of the cap ring. In one aspect, the lip 324 extends around about 30° of the periphery of the cap ring 304; however, the lip may extend longer or shorter distances around the periphery of the cap ring. The lip 324 is configured to receive the first, outer component 112 of the outer ring 110 such that the outer ring is positioned between the lip 324 and the gel pad 306 (see FIG. 16). More particularly, when the outer ring 110 of the surgical retractor 100 is received by the distal portion 314 of the cap ring 304, the outer ring of the surgical retractor embeds into the gel pad 306 at the distal portion of the cap ring and displaces the gel, thereby forming a seal between the gel pad and the outer ring and sleeve 106 of the surgical retractor. This places the gel pad 306 in juxtaposition with the incision 400 or body orifice.

In one aspect, the distal portion 314 of the cap ring 304 also includes a swinging lever 330 (FIG. 13) that swings on a plane that is substantially perpendicular to the axis 316 of the cap ring. In one aspect, the lever 330 is positioned substantially opposite the lip 324 on the distal portion 314 of the cap ring 304. The outer surface 332 of the cap ring 304 may include a lug 334 to which the lever 330 is coupled. In one aspect, the lug 334 includes an aperture 336 that extends substantially parallel to the longitudinal axis 316 of the cap ring 304 and is adapted to receive a hinge pin 338 portion of the lever 330. However, those with ordinary skill in the art will recognize that the hinge pin may be positioned on the lug and the aperture may be positioned in the lever. Also, other means that are well known in the art may be used to hinge the lever to the cap ring. When coupled to the cap ring 304, the lever 330 includes a proximal end 340 and a distal end 342. The lever 330 includes a first, distal substantially flat lip 344 positioned at the distal end 342 of the lever and lying in a plane that is positioned substantially perpendicular to the axis 346 of the pin 338 on the lever. It should be noted that the axis 346 of the pin 338 on the lever 330 is substantially parallel to the longitudinal axis 316 of the cap ring 304. The lever 330 may also include a second, proximal substantially flat lip 348 positioned at the proximal end 340 of the lever and also lying in a plane that is substantially perpendicular to an axis 346 of the pin 338 on the lever such that the proximal lip of the lever is substantially parallel to the distal lip 344 of the lever. Both of the distal and proximal lips 344, 348 of the lever 330 extend from the same side of the lever.

In a first, open state (FIG. 18), the lever 330 is swung outwardly, away from the body of the cap ring 304 to provide clearance for inserting the outer ring 110 of the surgical retractor 100 into the gel cap. In a second, closed state (FIG. 19), the lever 330 is swung toward the cap ring 304 such that the distal and proximal lips 344, 348 of the lever protrude radially inwardly from the body of the lever and radially inwardly through the wall 328 of the cap ring. In one aspect, the wall 328 of the distal portion 314 of the cap ring 304 includes a first aperture 350 or groove for receiving the distal lip 344 of the lever 330. Similarly, the wall 328 of the distal portion 314 of the cap ring 304 also includes a second aperture 352, such as a slot, for receiving and supporting the proximal lip 348 of the lever 330. In one aspect, the distal lip 344 on the lever 330 extends around about 60° of the periphery of the cap ring and the proximal lip 348 on the lever extends around about 45° of the periphery of the cap ring; however, the distal and proximal lips may extend longer or shorter distances around the periphery of the cap ring.

Figure 20:
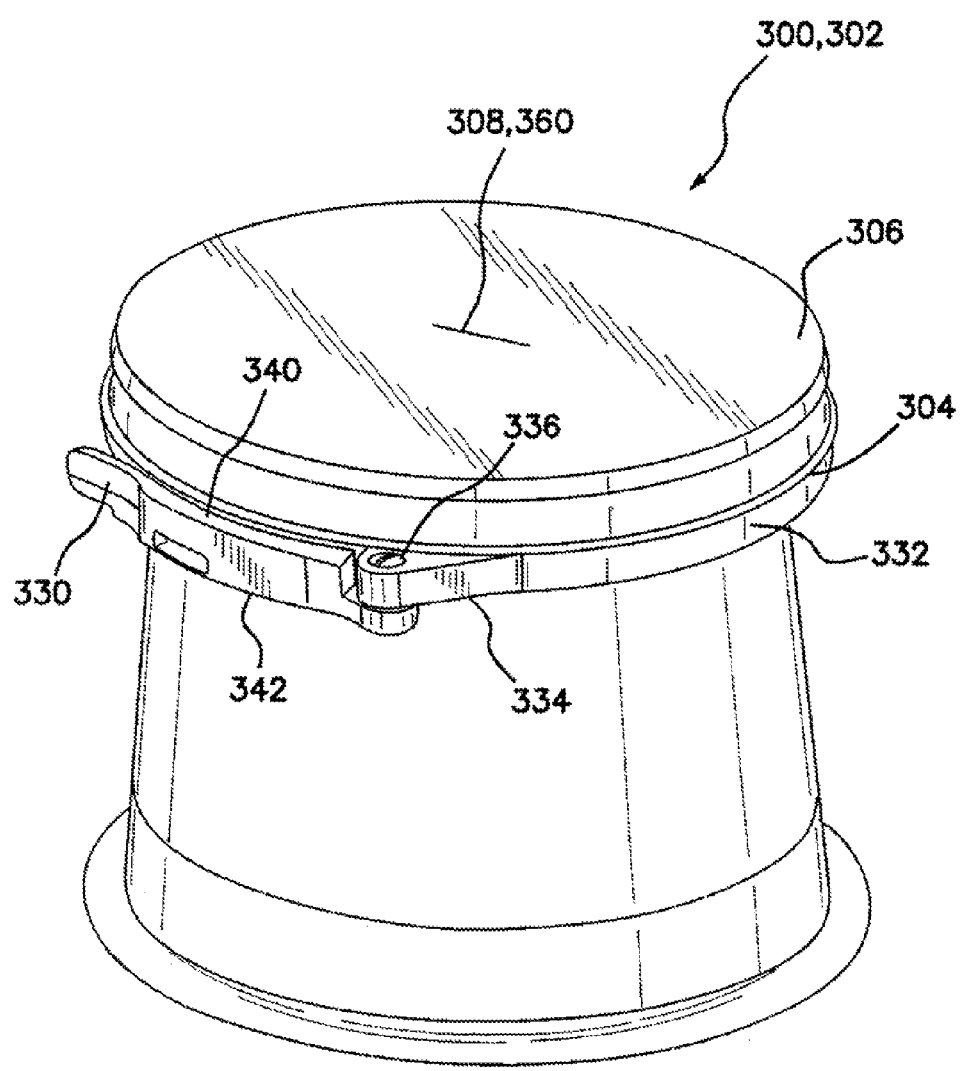
FIG. 20 is a perspective view of a surgical retractor with a gel cap in accordance with various aspects of the present invention.
Figure 21:
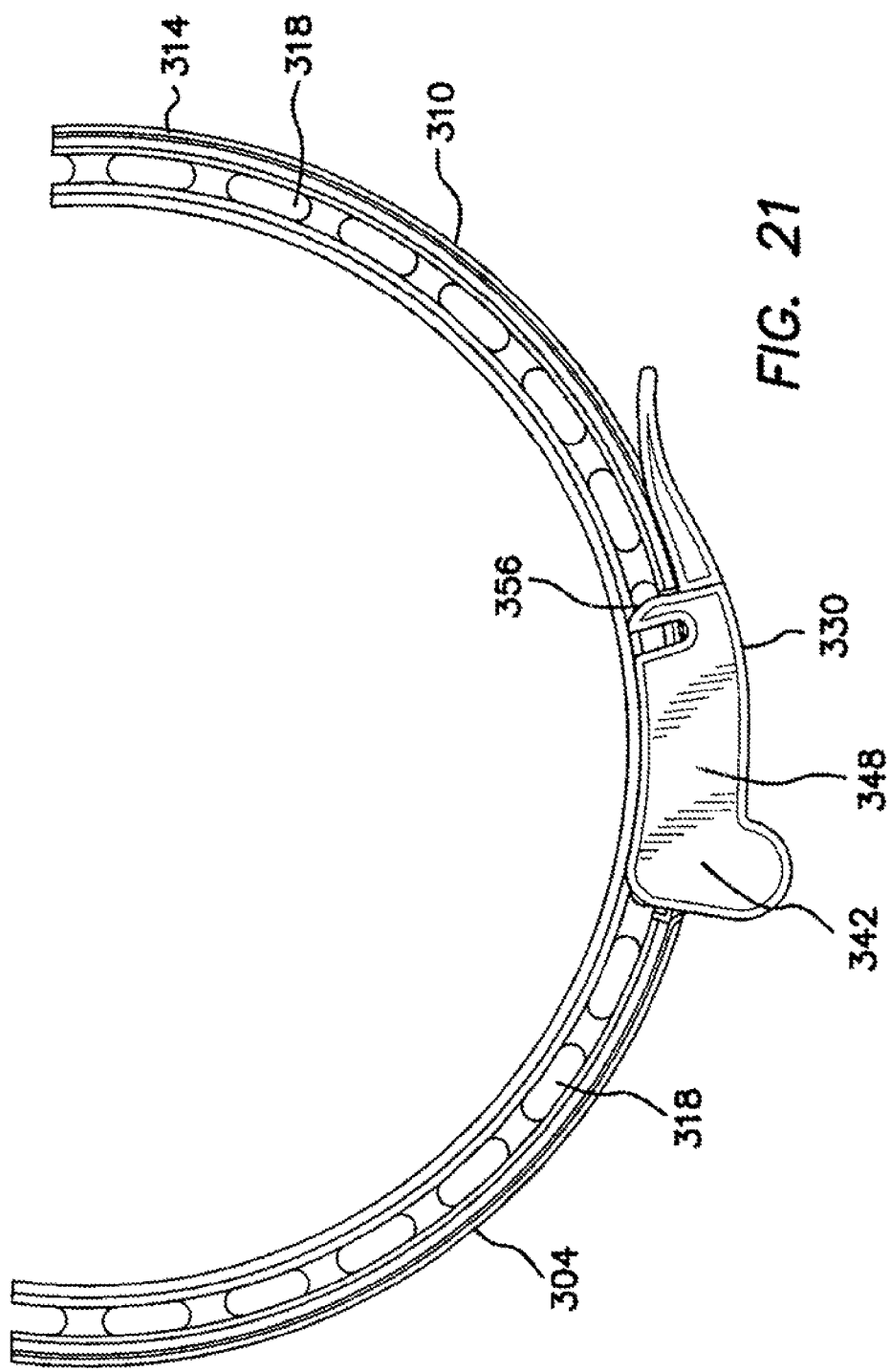
FIG. 21 is a partial bottom view of a cap ring portion of a gel cap for use with a surgical retractor in accordance with various aspects of the present invention.
Figure 22:
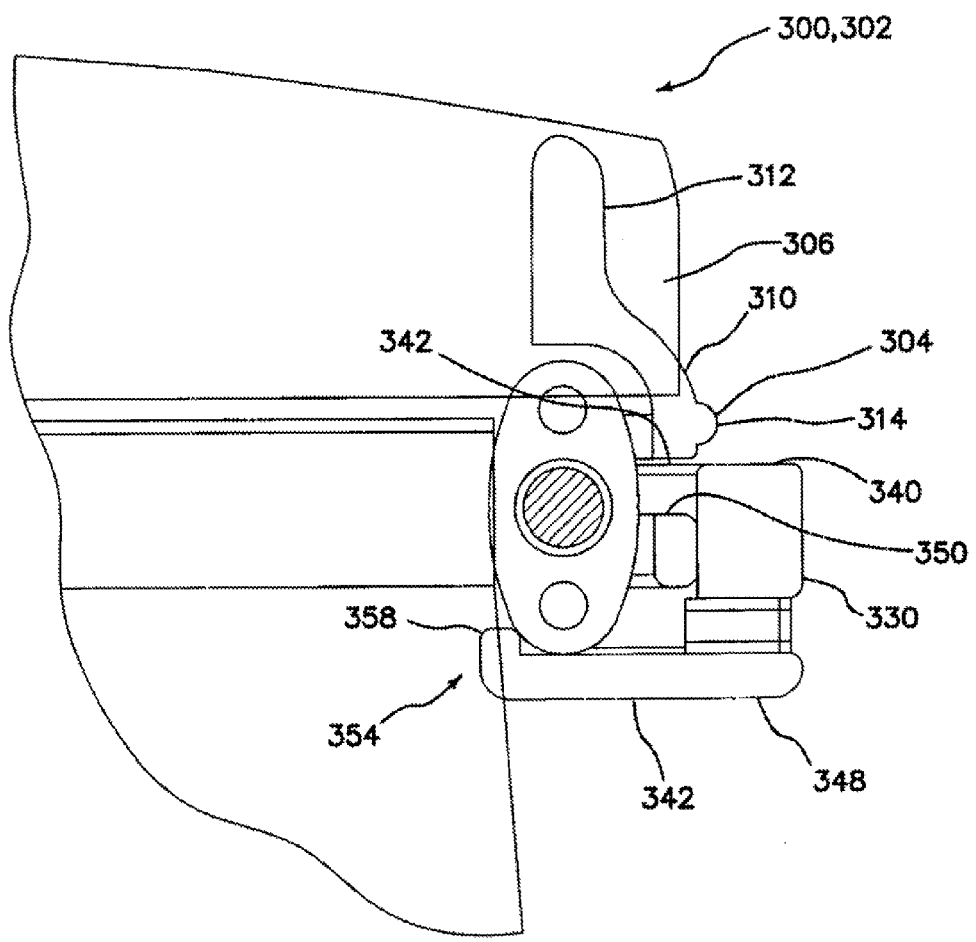
FIG. 22 is a side view, partially in cross section, of a surgical retractor and a gel cap in accordance with various aspects of the present invention.
Figure 23:
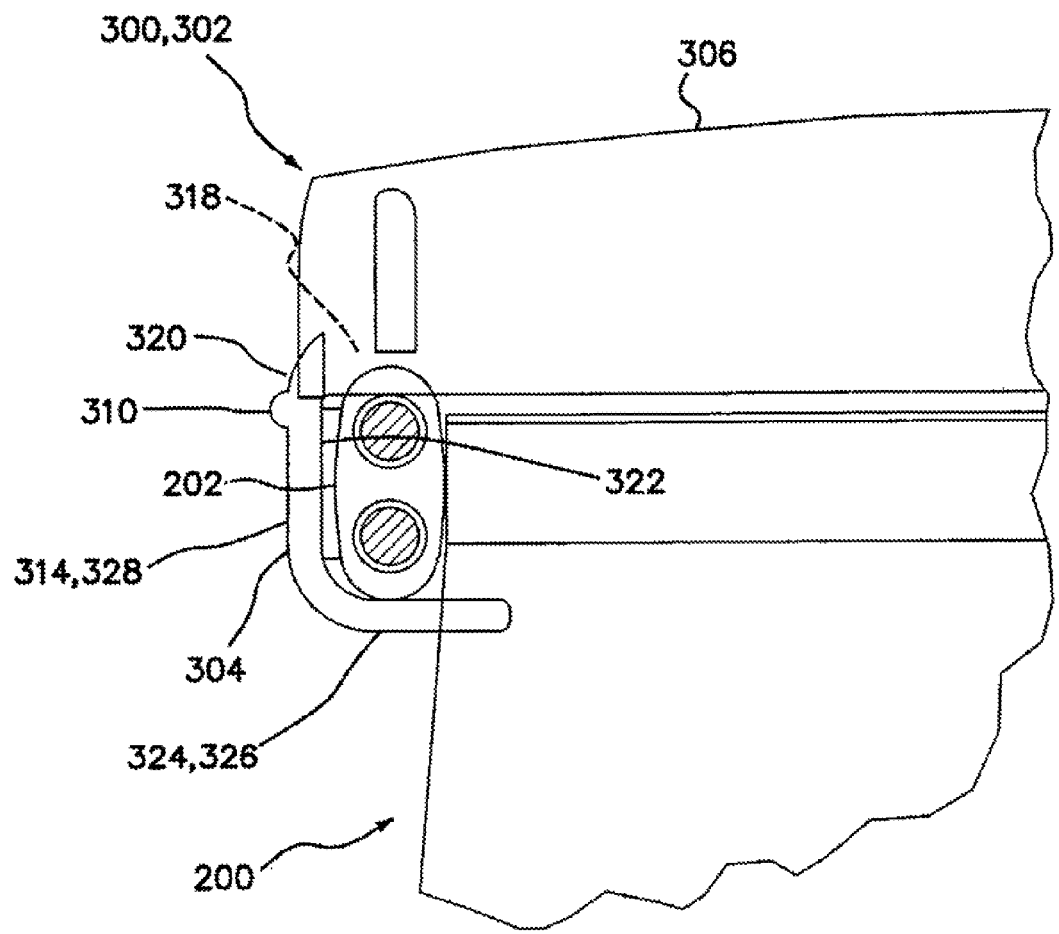
FIG. 23 is a side view, partially in cross section, of a surgical retractor and a gel cap in accordance with various aspects of the present invention.
Figure 24:
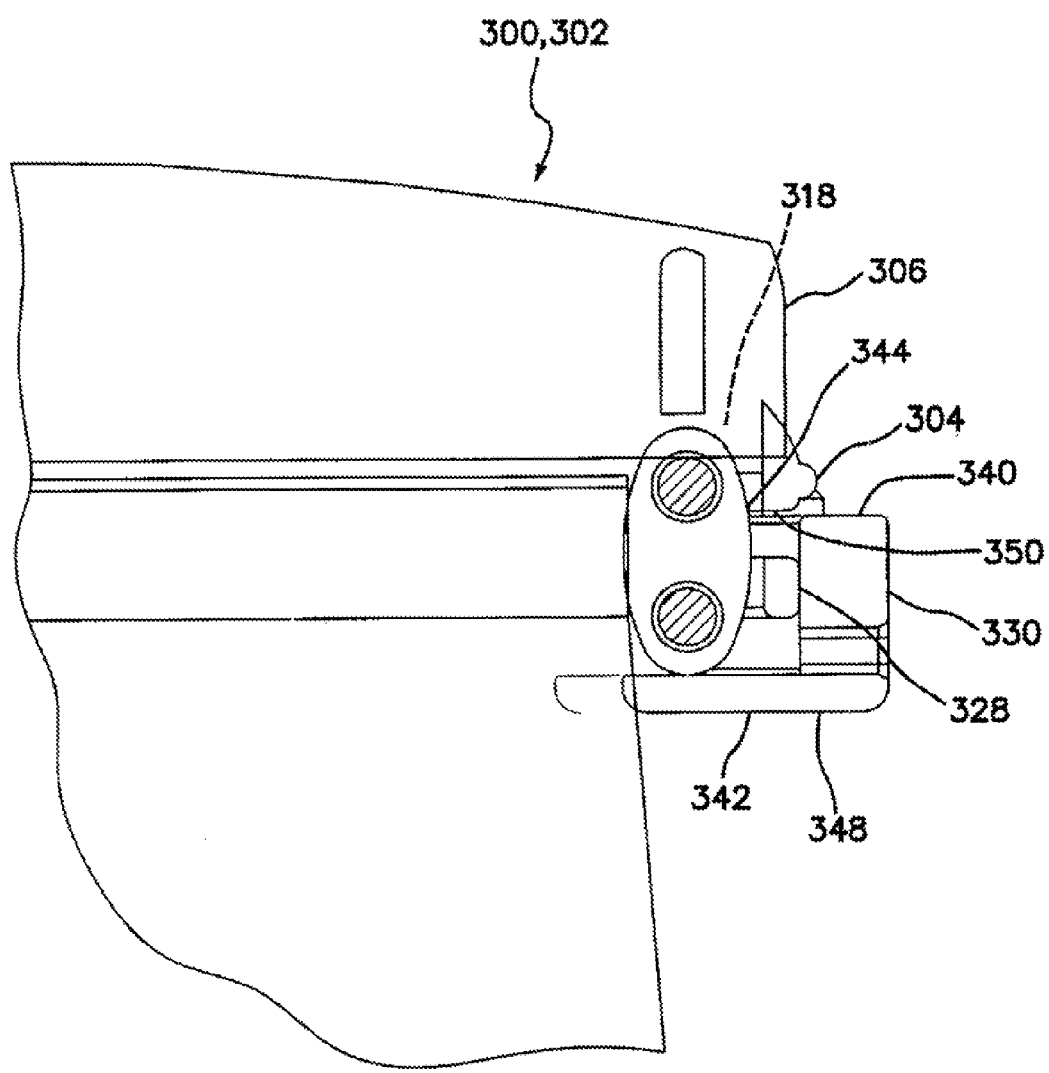
FIG. 24 is a side view, partially in cross section, of a surgical retractor and a gel cap in accordance with various aspects of the present invention.
Figure 25:
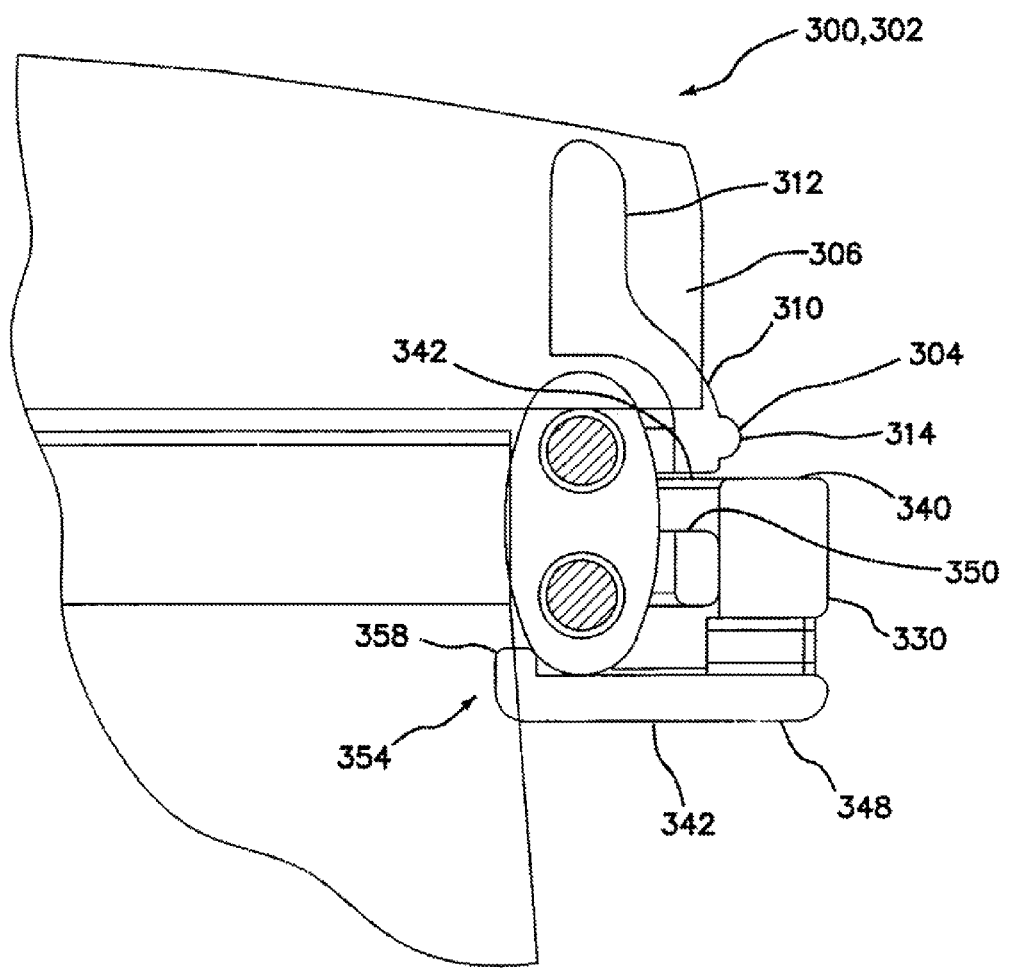
FIG. 25 is a side view, partially in cross section, of a surgical retractor and a gel cap in accordance with various aspects of the present invention.

The gel cap facilitates simple and rapid set-up. In use, the surgical retractor 100 is first used to retract the incision in the body wall of a patient, as described above. With the lever 330 in the first state, the gel cap 302 is brought to the outer ring 110 of the surgical retractor 100 at an angle with the lip portion 324 of the cap ring 304 toward the patient. The lip portion 324 of the cap ring is slid under the first, outer component of the outer ring 110, between the outer ring and the patient, and then the remainder of the gel cap 302 is swung onto the outer ring. The lever 330 is then swung closed into the second state (FIG. 20). In the second state, the distal lip 344 of the lever 330 abuts the distal surface of the first, outer component of the outer ring 110 of the surgical retractor 100 and secures the gel cap 302 to the surgical retractor (FIG. 22). More particularly, with the gel cap 302 mounted onto the outer ring 110 of the surgical retractor 100 and the lever 330 positioned in the second state, the lip portion 324 of the cap ring 304 and the distal lip 344 of the lever receive the outer ring of the surgical retractor. The outer ring 110 of the surgical retractor 100 is positioned between the lip portion 324 of the cap ring 304 and the distal lip 344 of the lever 330 at the distal end of the outer ring of the surgical retractor and the gel pad 306 at the proximal end of the outer ring of the surgical retractor.

The lever 330 includes locking means 354 (FIG. 17) to prevent unintended opening of the lever from the second state to the first state. In one aspect, to positively lock the lever 330 into the second state, one of the distal and proximal lips 344, 348 of the lever includes a latch 356 that engages the groove/aperture 350, 352 in the cap ring through which the lip protrudes (see FIG. 21). In another aspect, the distal lip 344 of the lever 330 includes a catch 358 (FIG. 22) protruding proximally to engage the distal surface of the first, outer component of the outer ring 110 of the surgical retractor 100 at a position on the inner periphery of the outer ring.

With the gel cap 302 mounted onto the outer ring 110 of the surgical retractor 100 and the lever 330 positioned in the second state, the proximal lip 348 on the lever positioned in the aperture 352 in the cap ring 304 provides support for the lever to counteract cantilever forces induced by the displaced gel of the gel pad 306. Support of the proximal lip 348 also helps the distal lip 344 maintain the position of the outer ring 110 of the surgical retractor 100 against the gel pad 306.

In another aspect, the gel cap 302 may include more than one lever 330 with the levers substantially equally spaced between each other and the lip 324 on the cap ring 304. In a further aspect, the lip 324 on the cap ring 304 may be omitted and at least two levers 330 used to secure the gel cap 302 to the surgical retractor 100. The at least two levers 330 may be substantially equally spaced about the periphery of the distal portion of the cap ring.

The gel cap 302 with the lip 324 and lever 330 on the cap ring is best suited for use with surgical retractors 100 having an outer ring 110 that is substantially rigid and noncompliant. If the outer ring 110 of the surgical retractor 100 were not rigid, the outer ring may tend to pull out of the gel cap 302, thereby compromising the seal between the gel pad 306 and the surgical retractor and potentially resulting in deflation of the insufflated body cavity.

The cap ring 304 in one aspect includes a polymer, e.g., polyethylene (PE). In one aspect, the polyethylene is a low density polyethylene (LDPE) or high density polyethylene (HDPE), or ultra high molecular weight polyethylene (UHMWPE). In one aspect, the cap ring 304 may be made of a polymer, such as polycarbonate and may be fabricated by methods including injection molding.

The gel pad 306 may be coupled to, attached to, formed or integrated with the cap ring 304 so that a gas-tight conduit is formed between the cap ring and the sleeve 106. The gel pad 306 covers and seals the entire opening in the cap ring 304. Additionally, in one aspect the gel pad 306 is adapted to cover substantially the entire wound 400 opening or body opening. As stated above, in one aspect the gel pad includes a plurality of intersecting dead-end slits 360, 362 that form an access portion or passage through the gel pad 306. The gel pad 306 provides a gas tight seal around a variety of shapes and sizes of hands or instruments inserted therethrough.

In one aspect, the gel material from which the gel pad 306 is made is an elastomeric gel. Some such gels have been described in U.S. patent application Ser. No. 10/381,220, filed Mar. 20, 2003, the disclosure of which is hereby incorporated by reference as if set forth in full herein. The gel can be prepared by mixing a triblock copolymer with a solvent for the midblocks. The endblocks are typically thermoplastic materials, such as styrene, and the midblocks are thermoset elastomers such as, ethylene/butylene, isoprene or butadiene; e.g., Styrene-Ethylene/Butylene-Styrene (SEBS), Styrene-Isoprene-Styrene (SIS), Styrene-Butadiene-Styrene (SBS). In one aspect, the solvent used is mineral oil. Upon heating this mixture or slurry, the midblocks are dissolved into the mineral oil and a network of the insoluble endblocks forms. The resulting network has enhanced elastomeric properties over the parent copolymer. In one aspect, the triblock copolymer used is KRATON G1651, which has a styrene to rubber ratio of 33/67. Once formed, the gel is substantially permanent and, by the nature of the endblocks, processable as thermoplastic elastomers henceforward. The mixture or slurry has a minimum temperature at which it becomes a gel, i.e., the minimum gelling temperature (MGT). This temperature, in one aspect, corresponds to the glass transition temperature of the thermoplastic endblock plus a few degrees. For example, the MGT for the mixture of KRATON G1651 and mineral oil is about 120° C. When the slurry reaches the MGT and the transformation to a gel state takes place, the gel becomes more transparent, thereby providing means for visually confirming when the transformation of the slurry to the gel state is substantially complete and that the gel may be cooled. In addition to triblocks, there are also diblock versions of the materials that may be used where Styrene is present at only one end of the formula, for example, Styrene-Ethylene/Butylene (SEB).

For a given mass of slurry to form into a complete gel, the entire mass of the slurry is heated to the MGT and remains heated at the MGT for sufficient time for the end blocks to form a matrix of interconnections. The slurry will continue to form into gel at temperatures above the MGT until the slurry/gel reaches temperatures at which the components within the slurry/gel begin to decompose or oxidize. For example, when the slurry/gel is heated at temperatures above 250° C., the mineral oil in the slurry/gel will begin to be volatile and oxidize. Oxidizing may cause the gel to turn brown and become oily.

The speed at which a given volume of slurry forms a gel is dependant on the speed with which the entire mass of slurry reaches the MGT. Also, with the application of temperatures higher than the MGT, this speed is further enhanced as the end block networks distribute and form more rapidly.

The various base formulas may also be alloyed with one another to achieve a variety of intermediate properties. For example, KRATON G1701X is a seventy percent (70%) SEB thirty percent (30%) SEBS mixture with an overall Styrene to rubber ratio of 28/72. It can be appreciated that an almost infinite number of combinations, alloys, and Styrene to rubber ratios can be formulated, each capable of providing advantages to a particular embodiment of the invention. These advantages will typically include low durometer, high elongation, and good tear strength.

It is contemplated that the gel material may also include silicone, soft urethanes and even harder plastics that might provide the desired sealing qualities with the addition of a foaming agent. The silicone material may be of the types currently used for electronic encapsulation. The harder plastics may include PVC, Isoprene, KRATON neat, and other KRATON/oil mixtures. In the KRATON/oil mixture, oils such as vegetable oils, petroleum oils and silicone oils may be substituted for the mineral oil.

Any of the gel materials contemplated could be modified to achieve different properties such as enhanced lubricity, appearance, and wound protection. Additives may be incorporated directly into the gel or applied as a surface treatment. Other compounds may be added to the gel to modify its physical properties or to assist in subsequent modification of the surface by providing bonding sites or a surface charge. Additionally, oil based colorants may be added to the slurry to create gels of different colors.

In one aspect, the mixture/slurry used with the various embodiments of the cap rings that are described herein are composed of about ninety percent (90%) by weight of mineral oil and about ten percent (10%) by weight of KRATON G1651. From a thermodynamic standpoint, this mixture behaves similar to mineral oil. Mineral oil has a considerable heat capacity and, therefore, at about 130° C. it can take three (3) or four (4) hours to heat a pound of the slurry sufficiently to form a homogeneous gel. Once formed, the gel can be cooled as quickly as practicable with no apparent deleterious effects on the gel. This cooling, in one aspect, is accomplished with cold-water immersion. In another aspect, the gel may be air-cooled. Those with ordinary skill in the art will recognize that other cooling techniques that are well known in the art may be employed and are contemplated as within the scope of the present invention.

Many of the properties of the KRATON/oil mixture will vary with adjustments in the weight ratio of the components. In general, the greater the percentage of mineral oil the less firm the mixture; the greater the percentage of KRATON, the more firm the mixture. If the resultant gel is too soft it can lead to excessive tenting or doming of the gel cap during surgery when a patient's abdominal cavity is insufflated. Excessive tenting or doming may cause the slits 360, 362 to open, providing a leak path. Additionally, if the gel is too soft it might not provide an adequate seal. However, the gel should be sufficiently soft to be comfortable for the surgeon while simultaneously providing good sealing both in the presence of an instrument and in the absence of an instrument.

If the slurry is permitted to sit for a prolonged period of time, the copolymer, such as KRATON, and the solvent, such as mineral oil, may separate. The slurry may be mixed, such as with high shear blades, to make the slurry more homogeneous. However, mixing the slurry may introduce or add air to the slurry. To remove air from the slurry, the slurry may be degassed. In one aspect, the slurry may be degassed in a vacuum, such as within a vacuum chamber. In one aspect, the applied vacuum may be 0.76 meters (29.9 inches) of mercury, or about one (1.0) atmosphere. The slurry may be stirred while the slurry is under vacuum to facilitate removal of the air. During degassing within a vacuum, the slurry typically expands, then bubbles, and then reduces in volume. The vacuum may be discontinued when the bubbling substantially ceases. Degassing the slurry in a vacuum chamber reduces the volume of the slurry by about ten percent (10%). Degassing the slurry helps reduce the potential of the finished gel to oxidize.

Degassing the slurry tends to make the resultant gel firmer. A degassed slurry composed of about 91.6% by weight of mineral oil and about 8.4% by weight of KRATON G1651, an eleven-to-one ratio, results in a gel having about the same firmness as a gel made from a slurry that is not degassed and that is composed of about ninety percent (90%) by weight of mineral oil and about ten percent (10%) by weight of KRATON G1651, a nine-to-one ratio.

Mineral oil is of a lighter density than KRATON and the two components will separate after mixing, with the lighter mineral oil rising to the top of the container. This separation may occur when attempting to form static slurry into gel over a period of several hours. The separation can cause the resulting gel to have a higher concentration of mineral oil at the top and a lower concentration at the bottom, e.g., a non-homogeneous gel. The speed of separation is a function of the depth or head height of the slurry being heated. The mass of slurry combined with the head height, the temperature at which the gel sets and the speed with which the energy can be transferred to the gel, factor into the determination or result of homogeneous gel versus a non-homogeneous gel.

The gel pad or gel cap in various aspects of the present invention may be gamma sterilized. The relative or comparative simplicity of qualifying the sterilization process, for example of gamma versus ethylene oxide, of the gel pad and the device with the gel pad is desirable. However, under gamma sterilization large bubbles can form in the gel pad causing potential cosmetic or aesthetic issues in the sterilized devices. The bubbles are more than ninety-nine percent (99%) room air, so removal of the dissolved air in the slurry is performed prior to forming the slurry into gel. For example, the slurry may be degassed via vacuum, as described above, and turned into gel by heat. Bubbles may still form in the gel during gamma sterilization but disappear in a period of about twenty-four (24) to seventy-two (72) hours. In one aspect, the percentage of dissolved gas in the mineral oil at room temperature is about ten percent (10%). The removal of the air in the gel has an additional effect of making the gel firmer. This however is counterbalanced by the softening effect on the gel caused by gamma radiation during gamma sterilization.

If the gel pad is to be gamma sterilized, the gel may include about ninety percent (90%) mineral oil by weight and about ten percent (10%) KRATON by weight. As stated above, degassing the slurry has the effect of making the gel firmer. However, the gamma radiation softens the gel to substantially the same firmness as a gel having about ninety percent (90%) mineral oil by weight and about ten percent (10%) KRATON by weight that is not degassed and gamma sterilized.

In one aspect, cyanoacrylate, e.g., SUPERGLUE or KRAZY GLUE, may be used to bond or otherwise couple or attach the gel pad 306 to the cap ring 304. The adhesive may attach to either the rubber or styrene component of the triblock and the bond is frequently stronger than the gel material itself. In another aspect, a solvent may be used to dissolve the plastics in the cap ring and the polystyrene in the gel pad. The solution of solvent is applied to the gel pad and cap ring in either a spray or dip form. In effect, the solution melts both the plastic of the cap ring as well as the polystyrene in the the gel pad to allow a chemical bond to form between the two, which remains when the solvent evaporates.

Polyethylene can be dissolved in mineral oil and then applied to the gel pad. The mineral oil will not evaporate but will over time absorb into the gel pad and impart a polyethylene layer on the gel pad that may have some beneficial properties.

In one aspect, the gel pad 306 is cast into a DYNAFLEX or KRATON polymer support structure, e.g., the cap ring 304. By using KRATON polymer or a similar material in the cap ring, ring adhesion between the gel pad 306 and the cap ring 304 can be achieved. The polystyrene in the gel pad 306 is identified as achieving adhesion with polyphenylene oxide (PPO), polystyrene and other polymers.

In the casting process, the gel pad 306 and the cap ring 304 are heated to a temperature above about 130° C. and held at that temperature for several hours, e.g., about three (3) to four (4) hours. The temperature used is not sufficient to deform the cap ring 304.

As stated above, in one aspect the cap ring 304 includes a polymer, e.g., polyethylene (PE). The gel includes mineral oil. PE has a higher molecular weight than mineral oil. PE is dissolved by mineral oil at high temperatures. As such, as the PE in the cap ring 304 and the mineral oil in the gel pad 306 intermix as both are heated to and held at temperatures above about 130° C., a bond between the PE and gel pad is formed.

In one aspect, the cap ring 304 includes polycarbonate. The polycarbonate of the cap ring 304 does not form bonds with the gel pad 306 at 130° C. However, by raising the temperature to about 150° C. for a few minutes during casting, bonding occurs between the gel pad 306 and the cap ring 304. As such, heating the gel pad 306 and cap ring 304 to temperatures at which both the polystyrene of the gel and the polycarbonate are simultaneously beyond their melt points allows bonds to form between the gel pad and the cap ring. Alternatively, the gel pad 306 and cap ring 304 may be heated to near or at the glass transition temperature of the polycarbonate cap ring to form the bond between the gel pad and the cap ring.

In one aspect, casting the gel pad 306 into the cap ring 304 to form a gel cap 302 includes placing the cap ring into a mold cavity of a casting mold. The mold cavity may include support for the annular walls of the cap ring 304. The mold may be made of aluminum, copper, brass, or other mold material having good heat dissipation properties. However, those with ordinary skill in the art will recognize that other mold materials having lower heat dissipation properties will produce acceptable parts and these are contemplated as within the scope of the present invention as well.

The mold cavity having the cap ring 304 is filled with the slurry such that the slurry is in contact with the cap ring. To facilitate filling voids in the mold cavity with the slurry, the slurry may be preheated, for example, to about 52° C. (125° F.). Preheating the slurry to a temperature below the MGT reduces the viscosity of the slurry and allows the slurry to flow more easily. As stated above, the slurry may have been degassed in a vacuum. The slurry may be degassed again within the mold after the mold cavity is filled to remove air that may have been introduced during the filling of the mold cavity and to facilitate flow of the slurry into voids in the mold. Heat is applied to the mold having the cap ring 304 and the slurry, such as in an oven, until the slurry attains a temperature of about 150° C. As stated above, the slurry turns into gel at about 120° C., however, at about 150° C., the gel can bond to a polycarbonate cap ring 304. Depending on the material used to fabricate the cap ring 304, bonding may take place at temperatures other than about 150° C. If the cap ring 304 is fabricated of a material having a lower melting point than 120° C., then the gel pad 306, such as a gel slug 306, may be molded separately and then bonded to the cap ring. The slits 360, 362 may be molded into the gel pad 306 through the use of an insert in the form of the slit in the mold.

Once the temperature of the gel pad 306 reaches about 150° C., the gel cap 302 may be cooled, such as by air-cooling, cold-water immersion, or other cooling means that are well known in the art. At 150° C. the gel pad is soft and if it were distorted during cooling it would set with the distortion included. To reduce the likelihood of distorting the gel pad 306, the gel cap 302 may be cooled within the mold. Cooling times may vary based on parameters including size and configuration of the mold, quantity of gel, temperature and quantity of cooling medium, cooling medium properties and the mold material. As an example, the cooling time may be about two (2) hours if cooling in air and about fifteen (15) minutes if cooling in water. Whether cooling with air or water, the final properties of the gel are substantially the same. The gel cap 302 is typically cooled to about ambient room temperature, but may be cooled to lower temperatures. If the gel cap 302 is cooled to about 0° C., then the gel will harden. This may be beneficial for other means of coupling the gel pad 306 to the cap ring 304, such as with a secondary operation. The gel cap 302 may be removed from the mold at any time after the gel has set.

When removed from the mold, the gel pad 306 typically has a tacky surface. The gel cap 302 may be coated with a powder, such as cornstarch, to substantially reduce or eliminate the tackiness of the cured gel pad 306.

As stated above, in another aspect, the gel pad 306 may be molded separately from the cap ring 304 and coupled to the cap ring by a secondary operation, such as by bonding. In one aspect, the gel pad 306 may be molded into a gel slug 306 having an outer perimeter smaller than the inner cylindrical wall of the cap ring 304 and to a height higher than the height of the cap ring. Since the gel pad 306 is being molded separate from the cap ring 304, the slurry only needs to be heated until it reaches about 120° C. and completes the transformation from slurry into gel and the gel becomes substantially transparent. The gel slug 306 may then be placed within the inner cylindrical wall of the cap ring 304. The gel slug 306 may be cooled, such as to about 0° C., prior to placing it within the inner cylindrical wall of the cap ring 304. The gel slug 306 may be coupled to the cap ring 304 through compression molding with the gel slug being compressed longitudinally so that the outer perimeter of the gel slug expands and compresses against the inner cylindrical wall of the cap ring. The gel slug 306 and cap ring 304 are heated to a sufficient temperature for the polystyrene of the gel and the polymer of the cap ring to form bonds between the gel and the cap ring. Molding the gel slug 306 separately from the cap ring 304 and heat bonding the gel slug to the cap ring at a later time is especially useful when the cap ring is made of a material that has a lower melting temperature than the MGT. In such situations, the gel slug 306 can be molded first and heat bonded to the cap ring 304 without melting the cap ring.

An advantage associated with the surgical access device is it enables a surgeon to quickly retract and protectively line an abdominal wall incision while being able to easily accommodate variations in abdominal wall thickness between patients. In addition, the device effectively seals around the interior and exterior of the incision, and allows a sealing cap to be coupled to the device to seal the abdominal cavity and to enable a laparoscopic procedure to be performed.

Many alterations and modifications may be made by those having ordinary skill in the art without departing from the spirit and scope of the invention. For these reasons, the above description should not be construed as limiting the invention, but should be interpreted as merely exemplary of the embodiments.

The invention claimed is:

1. A surgical access device, comprising:
 a surgical retractor for retracting an opening in a biological body, the surgical retractor having,
  a noncompliant outer ring having an annular axis and a lumen extending along the annular axis, the noncompliant outer ring being adapted for juxtaposition with an outer surface of the biological body,
  a wire having a split and ends at the split being aligned and in a non-overlapping relationship with each other with the wire being disposed within the lumen of the outer ring,
  a coupler disposed between the ends in the wire preventing overlap of the ends of the wire,
  an inner ring arranged to be positioned through the opening in the biological body and inside the biological body, and
  a sleeve coupling the outer ring to the inner ring, the sleeve being adapted to traverse the opening in the biological body, and
 a lid adapted for being coupled to the noncompliant outer ring of the surgical retractor;
 wherein the coupler comprises a base portion having a periphery that matches a periphery of a cross-section of the noncompliant outer ring and the coupler has a plurality of pins protruding from the base portion.

2. The access device of claim 1 wherein the outer ring is made of materials that allow the outer ring to be turned around its annular axis.

3. The access device of claim 1 wherein the sleeve further comprises a material that is flexible and impermeable to fluids and bacteria.

4. The access device of claim 1 wherein the inner ring is made of materials having sufficient hardness to retain the shape of the inner ring after insertion of the inner ring inside the biological body.

5. The access device of claim 1 wherein the lid further comprises:
   a gel cap, having,
      a cap ring adapted to be coupled to the outer ring of the surgical retractor, and,
      a gel pad coupled to the cap ring, the gel pad being made of a gel material.

6. The access device of claim 5 wherein the gel pad of the gel cap has an access portion for providing a passage from outside the biological body into a body cavity, the passage forming an instrument seal in the presence of an instrument inserted therethrough and a zero seal in the absence of an instrument inserted therethrough.

7. The access device of claim 5 wherein a distal portion of the cap ring is adapted to receive the outer ring of the surgical retractor such that the outer ring of the surgical retractor embeds into the gel pad and displaces the gel, thereby forming a seal between the gel pad and the outer ring and sleeve of the surgical retractor.

8. The surgical access device of claim 1 wherein the noncompliant outer ring has a split and ends at the split of the noncompliant outer ring are aligned and in a non-overlapping relationship with each other and wherein portions of the coupler extend into the ends of the noncompliant outer ring.

9. The surgical access device of claim 8 wherein the coupler is a monolithic structure and non-adjustable.

10. The access device of claim 1 wherein the plurality of pins are tapered.

11. The access device of claim 1 wherein the coupler has at least one tube portion protruding from the base portion.

12. The surgical access device of claim 1 wherein the coupler does not flex.

13. The surgical access device of claim 1 wherein the outer ring has a maximum width at a mid-section of the outer ring and the lumen of the outer ring is disposed at the mid-section of the outer ring.

14. A surgical access device, comprising:
   a surgical retractor for retracting an opening in a biological body, the surgical retractor having,
      a noncompliant outer ring having an annular axis and a lumen extending along the annular axis, the noncompliant outer ring being adapted for juxtaposition with an outer surface of the biological body,
      a wire having a split and ends at the split being aligned and in a non-overlapping relationship with each other with the wire being disposed within the lumen of the outer ring,
      a coupler disposed between the ends in the wire preventing overlap of the ends of the wire,
      an inner ring arranged to be positioned through the opening in the biological body and inside the biological body, and
      a sleeve coupling the outer ring to the inner ring, the sleeve being adapted to traverse the opening in the biological body, and
   a lid adapted for being coupled to the noncompliant outer ring of the surgical retractor;
   wherein the coupler comprises a base portion having a periphery that matches a periphery of a cross-section of the noncompliant outer ring;
   wherein the coupler has at least one tube portion protruding from the base portion;
   wherein the ends at the split of the wire includes a first end and a second end and the at least one tube portion includes a first tube portion and a second tube portion, the first tube portion arranged to receive the first end of the wire and the second tube portion arranged to receive the second end of the wire.

15. The access device of claim 14 wherein the first tube portion has a length arranged to maintain the first end of the wire within the first tube portion and the first tube portion within the lumen of the outer ring and wherein the second tube portion has a length arranged to maintain the second end of the wire within the second tube portion and the second tube portion within the lumen of the outer ring.

16. A surgical access device, comprising:
   a surgical retractor for retracting an opening in a biological body, the surgical retractor having,
      a noncompliant outer ring having an annular axis and a lumen extending along the annular axis, the noncompliant outer ring being adapted for juxtaposition with an outer surface of the biological body,
      a wire having a split and ends at the split being aligned and in a non-overlapping relationship with each other with the wire being disposed within the lumen of the outer ring,
      a coupler disposed between the ends in the wire preventing overlap of the ends of the wire,
      an inner ring arranged to be positioned through the opening in the biological body and inside the biological body, and
      a sleeve coupling the outer ring to the inner ring, the sleeve being adapted to traverse the opening in the biological body, and
   a lid adapted for being coupled to the noncompliant outer ring of the surgical retractor;
   wherein the ends at the split of the wire includes a first end and a second end and the coupler includes a first end and a second end, wherein the first end of the wire is inserted into the first end of the coupler and the second end of the wire is inserted into the second end of the coupler.

17. The surgical access device of claim 16 wherein the first end of the coupler is crimped onto the first end of the wire and the second end of the coupler is crimped onto the second end of the wire.

18. The surgical access device of claim 17 wherein the coupler is a metal tube and the wire is made of stainless steel.

19. A surgical access device, comprising:
   a surgical retractor arranged to retract an opening in a biological body, the surgical retractor having,
      a noncompliant outer ring having a top lumen and a bottom lumen, the noncompliant outer ring being adapted for juxtaposition with an outer surface of the biological body,
      a first wire having a split and ends at the split being aligned and in a non-overlapping relationship with each other with the first wire being disposed within the top lumen of the outer ring,
      a second wire having a split and ends at the split being aligned and in a non-overlapping relationship with each other with the second wire being disposed within the bottom lumen of the outer ring,
      a coupler disposed between the ends of the first wire and the ends of the second wire preventing overlap of the ends of the first wire with each other and preventing overlap of the ends of the second wire with each other,
      an inner ring arranged to be positioned through the opening in the biological body and inside the biological body, and a sleeve coupling the outer ring to the inner ring, the sleeve being adapted to traverse the opening in the biological body, and a lid adapted for being coupled to the noncompliant outer ring of the surgical retractor.

20. The surgical access device of claim 19 wherein the outer ring has a maximum width at a mid-section of the outer ring and the first wire is disposed above the mid-section of the outer ring and the second wire is disposed below the mid-section of the outer ring.

21. The access device of claim 19 wherein the top lumen has a first end and a second end, the bottom lumen has a first end and a second end and the coupler includes a first coupler and a second coupler, the first coupler connects the first end of the top lumen to the second end of the top lumen together in a snap-fit relationship and the second coupler connects the first end of the bottom lumen to the second end of the bottom lumen together in a snap-fit relationship.

22. The surgical access device of claim 19 wherein the ends at the split of the first wire includes a first end and a second end and the coupler includes a first end and a second end, wherein the first end of the first wire is inserted into the first end of the coupler and the second end of the first wire is inserted into the second end of the coupler.

23. The surgical access device of claim 22 wherein the first end of the coupler is crimped onto the first end of the first wire and the second end of the coupler is crimped onto the second end of the first wire.

24. The surgical access device of claim 23 wherein the ends at the split of the second wire includes a first end and a second end and the coupler is a first coupler and further comprising a second coupler, wherein the first end of the second wire is inserted into the first end of the second coupler and the second end of the second wire is inserted into the second end of the second coupler.

25. A surgical access device, comprising:
  a surgical retractor arranged to retract an opening in a biological body, the surgical retractor having,
    an outer ring having a split and ends at the split being aligned and in a non-overlapping relationship with each other, the outer ring having a top lumen, a middle lumen and a bottom lumen and the outer ring being arranged to be positioned juxtaposition with an outer surface of the biological body,
    a wire having a split and ends at the split being aligned and in a non-overlapping relationship with each other with the wire being disposed within the middle lumen of the outer ring,
    a coupler disposed between the ends in the wire preventing overlap of the ends of the wire and the coupler being disposed between the ends in the outer ring preventing overlap of the ends of the outer ring,
    an inner ring arranged to be positioned through the opening in the biological body and inside the biological body, and
    a sleeve connecting the outer ring to the inner ring, and
  a lid adapted for being coupled to the outer ring of the surgical retractor;
  wherein the ends at the split of the wire includes a first end and a second end and the coupler includes a first end and a second end, wherein the first end of the wire is inserted into the first end of the coupler and the second end of the wire is inserted into the second end of the coupler.

26. The surgical access device of claim 25 wherein the middle lumen of the outer ring has a diameter greater than a diameter of the top lumen and the diameter of the middle lumen is greater than a diameter of the bottom lumen.

27. The surgical access device of claim 25 wherein the outer ring has a maximum width at a mid-section of the outer ring and the middle lumen of the outer ring is disposed at the mid-section of the outer ring.

28. A surgical access device, comprising:
  a surgical retractor arranged to retract an opening in a biological body, the surgical retractor having,
    an outer ring having a split and ends at the split being aligned and in a non-overlapping relationship with each other, the outer ring having a top lumen, a middle lumen and a bottom lumen and the outer ring being arranged to be positioned juxtaposition with an outer surface of the biological body,
    a wire having a split and ends at the split being aligned and in a non-overlapping relationship with each other with the wire being disposed within the middle lumen of the outer ring,
    a coupler disposed between the ends in the wire preventing overlap of the ends of the wire and the coupler being disposed between the ends in the outer ring preventing overlap of the ends of the outer ring,
    an inner ring arranged to be positioned through the opening in the biological body and inside the biological body, and
    a sleeve connecting the outer ring to the inner ring, and
  a lid adapted for being coupled to the outer ring of the surgical retractor;
  wherein the coupler includes a base portion, a first pin protruding from the base portion, and a second pin protruding from the base portion, the first pin connected to the top lumen of the outer ring and the second pin connected to the top lumen or the bottom lumen of the outer ring.

29. The access device of claim 28 wherein the first pin and the second pin include barbs.

30. The surgical access device of claim 28 wherein the ends at the split of the wire includes a first end and a second end and the coupler includes a first end and a second end, wherein the first end of the wire is inserted into the first end of the coupler and the second end of the wire is inserted into the second end of the coupler.

* * * * *